US008922226B2

(12) United States Patent
Maher et al.

(10) Patent No.: US 8,922,226 B2
(45) Date of Patent: Dec. 30, 2014

(54) PRODUCTION LINE DETECTION APPARATUS AND METHOD

(75) Inventors: Anthony John Maher, Vermont South (AU); Lachlan John Maher, Mount Evelyn (AU); Cameron Anthony Maher, Vermont South (AU)

(73) Assignee: Detection Systems Pty Ltd, Bayswater Vic (AU)

( * ) Notice: Subject to any disclaimer, the term of this patent is extended or adjusted under 35 U.S.C. 154(b) by 960 days.

(21) Appl. No.: 12/439,600

(22) PCT Filed: Aug. 28, 2007

(86) PCT No.: PCT/AU2007/001236
§ 371 (c)(1),
(2), (4) Date: Jul. 9, 2009

(87) PCT Pub. No.: WO2008/025063
PCT Pub. Date: Mar. 6, 2008

(65) Prior Publication Data
US 2010/0013500 A1    Jan. 21, 2010

(30) Foreign Application Priority Data

Aug. 28, 2006   (AU) ................................. 2006904681
Sep. 1, 2006    (AU) ................................. 2006904769
Apr. 4, 2007    (AU) ................................. 2007901780

(51) Int. Cl.
*G01R 27/26*   (2006.01)
*G01N 27/22*   (2006.01)
*B65B 57/10*   (2006.01)

(52) U.S. Cl.
CPC ................ *G01N 27/22* (2013.01); *B65B 57/10* (2013.01)

USPC ............................. 324/663; 324/658; 324/686

(58) Field of Classification Search
USPC .................. 324/671, 672, 659, 663, 658, 686
See application file for complete search history.

(56) References Cited

U.S. PATENT DOCUMENTS

| 2,999,589 A | 9/1961 | Norwich |
| 3,938,113 A * | 2/1976 | Dobson et al. ........... 340/870.37 |
| 4,423,628 A | 1/1984 | Richter |

(Continued)

FOREIGN PATENT DOCUMENTS

| DE | 3417338 A1 | 11/1985 |
| DE | 4217359 A1 | 2/1993 |

(Continued)

OTHER PUBLICATIONS

Search Report issued in corresponding European Patent Application No. 12194094.4 dated Jan. 7, 2013.

*Primary Examiner* — Richard Isla Rodas
(74) *Attorney, Agent, or Firm* — Sughrue Mion, PLLC

(57) ABSTRACT

The present invention relates to the field of detection apparatus and/or methods. One aspect relates to an apparatus and/or detection methods for sensing material and/or detection of a predetermined characteristic within a detection zone. Another aspect relates to a method for improving the accuracy of an inspection device by capturing the human interpretation of its classification decision. Still another aspect relates to detection of relatively hard to detect items, for example items inside sealed packages. In a further aspect, the invention relates to a method of monitoring and/or improving the operation of a detection apparatus in which a detection result is obtained, and an adjustment (if necessary) is made in accordance with a comparison.

14 Claims, 29 Drawing Sheets

(56) References Cited

U.S. PATENT DOCUMENTS

| | | | |
|---|---|---|---|
| 4,563,635 A * | 1/1986 | Wagner et al. | 324/688 |
| 4,752,727 A * | 6/1988 | Schneider | 324/605 |
| 4,976,154 A * | 12/1990 | Schneider et al. | 73/861.06 |
| 5,134,379 A | 7/1992 | Maher et al. | |
| 5,166,679 A * | 11/1992 | Vranish et al. | 340/870.37 |
| 5,198,777 A * | 3/1993 | Masuda et al. | 324/671 |
| 5,394,095 A | 2/1995 | Kespohl | |
| 5,675,259 A | 10/1997 | Arndt et al. | |
| 5,854,683 A | 12/1998 | Keane | |
| 5,896,032 A * | 4/1999 | Yagi et al. | 324/660 |
| 5,932,806 A | 8/1999 | Rose et al. | |
| 5,966,018 A | 10/1999 | Edmunds et al. | |
| 6,025,726 A * | 2/2000 | Gershenfeld et al. | 324/671 |
| 6,043,743 A * | 3/2000 | Saito et al. | 340/562 |
| 6,158,768 A * | 12/2000 | Steffens et al. | 280/735 |
| 6,181,372 B1 | 1/2001 | Neri et al. | |
| 6,486,680 B1 * | 11/2002 | Mull | 324/662 |
| 6,574,540 B2 * | 6/2003 | Yokota et al. | 701/45 |
| 6,577,142 B2 * | 6/2003 | Eisenmann et al. | 324/674 |
| 6,771,913 B2 * | 8/2004 | Jeschonek et al. | 399/49 |
| 7,401,532 B2 * | 7/2008 | Wanami | 73/862.626 |
| 2003/0091355 A1 | 5/2003 | Jeschonek et al. | |
| 2005/0140378 A1 | 6/2005 | Hirota et al. | |

FOREIGN PATENT DOCUMENTS

| | | |
|---|---|---|
| EP | 0302727 A2 | 2/1989 |
| EP | 0330495 A2 | 8/1989 |
| EP | 0343928 A2 | 11/1989 |
| EP | 1102062 A2 | 5/2001 |
| EP | 1469307 A2 | 10/2004 |
| JP | 4328413 A | 11/1992 |
| JP | 2005017003 A | 1/2005 |
| JP | 2005017004 A | 1/2005 |
| WO | 2007/042139 A1 | 4/2007 |
| WO | 2007042139 A1 | 4/2007 |

* cited by examiner

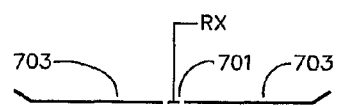
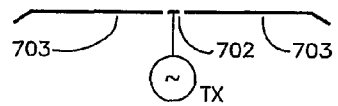
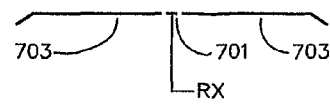
Figure 7a                    Figure 7b
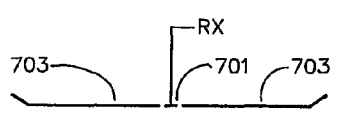
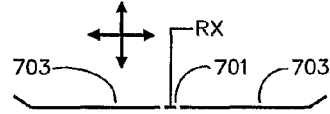
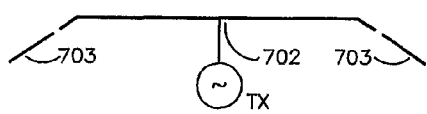
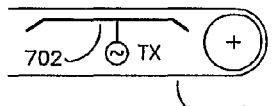
Figure 7c                    Figure 7d
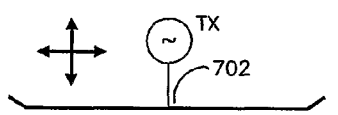
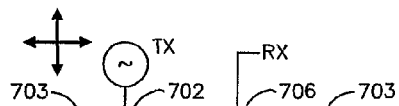
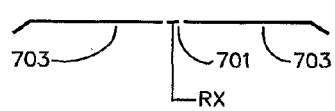
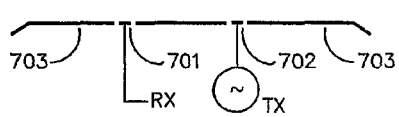
Figure 7e                    Figure 7f
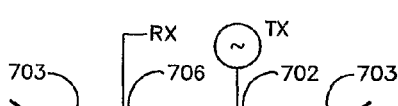
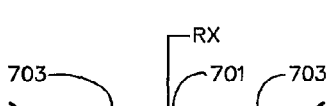
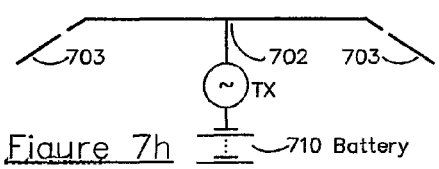
Figure 7g                    Figure 7h

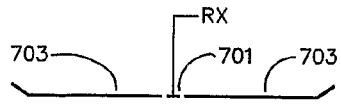
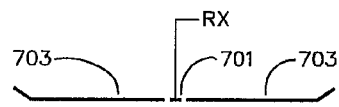
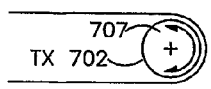
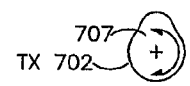
Figure 7i
Figure 7j
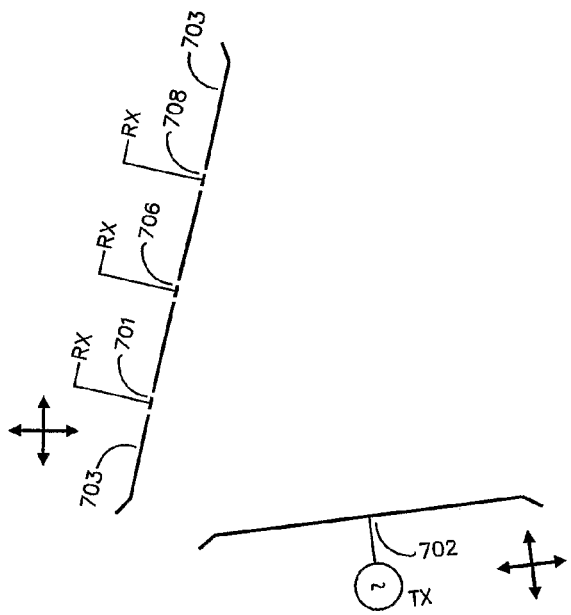
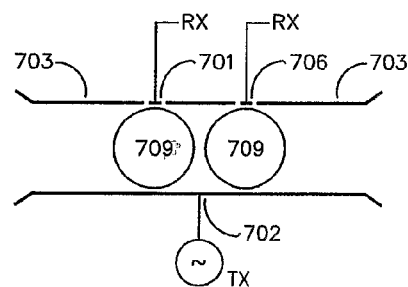
Figure 7k
Figure 7L
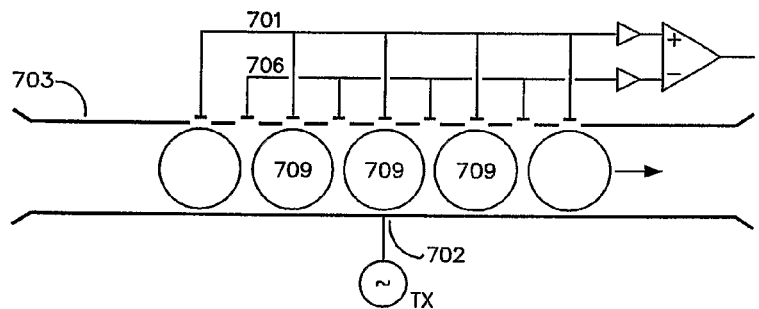
Figure 7m

PRODUCTION LINE DETECTION APPARATUS AND METHOD

FIELD OF INVENTION

The present invention relates to the field of detection apparatus and/or methods.

In one form, an aspect of invention relates to an apparatus and/or detection method for sensing material and/or detection of a predetermined characteristic within a detection zone. For example, the characteristic may be presence or absence of a material and/or the amount or density of a material.

In another form, an aspect of invention relates to a method and/or apparatus for improving the accuracy of an inspection device.

In still another form, an aspect of invention relates to the detection of relatively hard to detect targets, for example items inside sealed packages.

In yet a further form, an aspect of invention relates to apparatus and method(s) for inspecting products for quality defects. One example application is the inspection of the fill level of contents of containers or packages, such as liquids or tablets in bottles, as they pass down a conveyor.

It will be convenient to hereinafter describe the invention in relation to detection of a predetermined characteristic, however it should be appreciated that the present invention is not limited to that use only.

BACKGROUND ART

The discussion throughout this specification comes about due to the realisation of the inventors and/or the identification of certain prior art problems by the inventors.

There is a general need in the manufacture of certain goods to provide inspection of as much production line product as possible. This enables manufacturers to reduce waste and the number of faulty products reaching customers, enhances the manufacturer's reputation whilst reducing the cost of dealing with customer complaints or product liability problems and/or addresses regulation and/or compliance issues, such as the correct inclusion of contents into packages.

Traditional inspection techniques which rely on checkweighers, vision systems, x-ray, ultrasonic, gamma ray and capacitive inspection systems usually occupying a finite amount of production line space (length). Many such systems are considered to be relatively bulky with the result that installation of inspection systems into existing production lines is often very difficult. Furthermore, whilst some systems cannot inspect inside sealed packages, some other systems are unable to reliably inspect inside sealed packs.

Any discussion of documents, devices, acts or knowledge in this specification is included to explain the context of the invention. It should not be taken as an admission that any of the material forms a part of the prior art base or the common general knowledge in the relevant art in Australia or elsewhere on or before the priority date of the disclosure and claims herein.

An object of the present invention is to provide an improved inspection apparatus and/or method.

It is a further object of the embodiments described herein to overcome or alleviate at least one of the above noted drawbacks of related art systems or to at least provide a useful alternative to related art systems.

SUMMARY OF INVENTION

In a first aspect of embodiments described herein there is provided an apparatus and detection methods for sensing the amount of material between two plates, moving relative to one another. Preferably the detection uses a linearised capacitance measurement. A portable sensor is also contemplated according to an embodiment of the present invention. One application for the present invention is for sensing the amount of product inside sealed cartons as they are conveyed using a robotic head.

In a second aspect of embodiments described herein there is provided a detection apparatus and/or method comprising a first portion being a signal source or a signal receiver, a second portion being a signal receiver or a signal source, the first portion being disposed at an angle relative to the second portion and the first and second portions are disposed to provide, operatively, a detection zone.

Preferably, a characteristic or characteristic(s) of material in detection zone is detected.

Preferably, an example of a characteristic is, without limitation:

Presence/absence—of an item, target or of a component, whether in its entirety or a portion thereof
Count (of items normally in an ordered array)
Fill level/Head Space (air between top of fill and the foil lid or cap)
Location/Registration (e.g. in flow wrapping, the location of the bar relative to the crimped ends of the wrap)
Orientation (find items rotated 90 degrees)
Shape/Profile (profile confectionery bar, or of foil packaging tetra pack for example)
Integrity (not mangled or distorted)
Integrity of conductivity, data or frequency
Indicia
Density/Electrical Permittivity/Conductivity
Bridging (fill that has bridged from the top of the normal fill level up to the foil lid along a sidewall, for instance)
Isolation (ensure items are electrically independent)
Leaking (by virtue of bridging/isolation/shape described above),
Conductivity, resistance, capacitance, and/or impedance and
Other physical attributes as may be determined by the particular application and/or from time to time.

In a third aspect of embodiments described herein there is provided a detection apparatus and/or method comprising a first portion being a signal source or a signal receiver, a second portion being a signal receiver or a signal source, respectively, the first portion being movable with respect to the second portion, and the first and second portions, when in proximity to each other, being operatively adapted to provide a detection zone.

In a fourth aspect of embodiments described herein there is provided a method of providing detection of a characteristic of material and/or associated apparatus, comprising providing a first portion being a signal source or a signal receiver, providing a second portion being a signal receiver or a signal source, enabling the first portion to be disposed at an angle relative to the second portion and enabling the first and second portions to be disposed to provide, operatively, a detection zone.

In a fifth aspect of embodiments described herein there is provided a method of and/or apparatus for monitoring and/or improving the operation of a detection apparatus, comprising conducting a first detection using a detection apparatus, recording the result of the first detection, conducting a second detection on an entity which has already had a first detection, comparing the result obtained in the first and second detections and adjusting (if necessary) the detection apparatus in accordance with the comparison. The second detection can be performed by human (manual inspection), or by machine using the same or different inspection technique.

The present invention also describes a method for improving the accuracy of an inspection device by capturing the human interpretation of its classification decision.

In a sixth aspect of embodiments described herein there is provided a method of and/or apparatus for detecting a characteristic of a target associated a package, comprising the steps of scanning the package, obtaining an output resultant from the step of scanning, and analysing at least a portion the output to determine the characteristic. Preferably, the characteristic is the presence of a target.

In a seventh aspect of embodiments described herein there Is provided a method of monitoring and/or improving the operation of a detection apparatus and/or associated apparatus, comprising conducting a first detection using a detection apparatus, determining whether the first detection included lateral movement of the item or product being detected and correlating the first detection with the lateral movement determination.

The various scanning topologies, apparatus and/or method(s) as disclosed herein may be applicable to capacitive, x-ray, gamma ray, quadrapole resonance, radio frequency spectroscopy and/or any other form of detection technology.

A package may be scanned a number of times in accordance with the present invention, for example to provided additional verification of detection results, provide one or more electrode configurations (enabling the sensing and/or detection of various material, location and/or positioning of material) and/or to account for various possible orientations of package(s) and it's contents.

A characteristic, resultant waveform, output and/or signal obtained by virtue of application of the present invention(s) may be indicative or quantitative. Further processing of the result may or may not be required, dependant on the particular application of the present invention(s).

Other aspects and preferred aspects are disclosed in the specification and/or defined in the appended claims, forming a part of the description of the invention.

In essence, one aspect of the present invention comes about by the realisation that the electrodes which usually form a head in a detection apparatus do not have to be fixed. Thus, one or both heads according to the present invention may be movable relative to one another, product line equipment and/or relative to a product to be scanned. Another aspect of invention comes about by realising that a feedback feature can be utilised in providing enhanced accuracy of detection method(s) and/or apparatus. A still another aspect of invention comes about in essence due to the realisation that a characteristic of a target can be detected in one or any combination of a number of ways, including scanning, target doping, sensing characteristic and/or characteristic contrast.

In essence, another aspect of invention comes about due to the realisation that, whilst prior art apparatus, such as the apparatus disclosed U.S. Pat. No. 5,134,379 by present inventors, have the transmitting and receiving electrodes located opposite each other, in this invention, the electrode(s) may be arranged relatively parallel, perpendicular or at any angle to each other. It has been found that the orientation and proximity of the receiver electrode(s) has a substantial effect on the performance of the detection device.

Throughout this specification, 'product' may include 'material' and visa versa. Product and/or material may refer to any entity, physical property or characteristic of a product or material.

Throughout this specification, 'package' includes, for example, reference to any form of container, enclosure, pouch, sachet, carton, box, pack, show box, case, tray, pallet, shipping case (shipper), crate, vessel, wrapping, whether sealed or unsealed, and may be made of any material.

The present invention has been found to result in a number of advantages, such as The ability to inspect inside sealed packs, cartons or containers The ability to inspect without x-ray or gamma radiation The ability to focus on individual products, components, targets and/or characteristics of targets, products or components to improve accuracy Detection of crushed, mangled or displaced items that check weighers miss Able to reliably inspect multiple layers of product.

Fast—speed typically only limited by speed at which product can be conveyed and reliably rejected.

There is a greatly reduced installation requirement, as the equipment can be installed in some cases 'over the top' of an existing production line.

Relative immunity to variations in light sources

Relative immunity to variations in package optical density and colour

Relative immunity to packaging graphics

Relative immunity to labels and tamper proof sleeves, if desired

The ability to detect relatively hard to detect items

Relatively nonlinear in an advantageous way (especially for liquid fill level)

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limitative of the present invention, and In which:

FIGS. 7a to 7m illustrate a number of electrode configurations, without limitation, according to an embodiment of the present invention.

DETAILED DESCRIPTION

Throughout the specification including the drawings, the various electrodes shown would in practice have a linearising surface provided at or near the same potential, for example by having a suitable proximate ground plane. The effect of this is to enhance linearity of the field, for example as disclosed in U.S. Pat. No. 5,134,379 also by the present inventor(s). Further effects may be gained, such as to reduce to effect of stray fields and/or attenuate interference. Preferably, the field should be substantially linear. Often the electrode could be substantially surrounded by the linearising surface except for the 'active' surface (transmitting or receiving).

Throughout the specification, although any field may be used, for the various embodiments disclosed the field is preferably a substantially linearised field.

Figure 1:
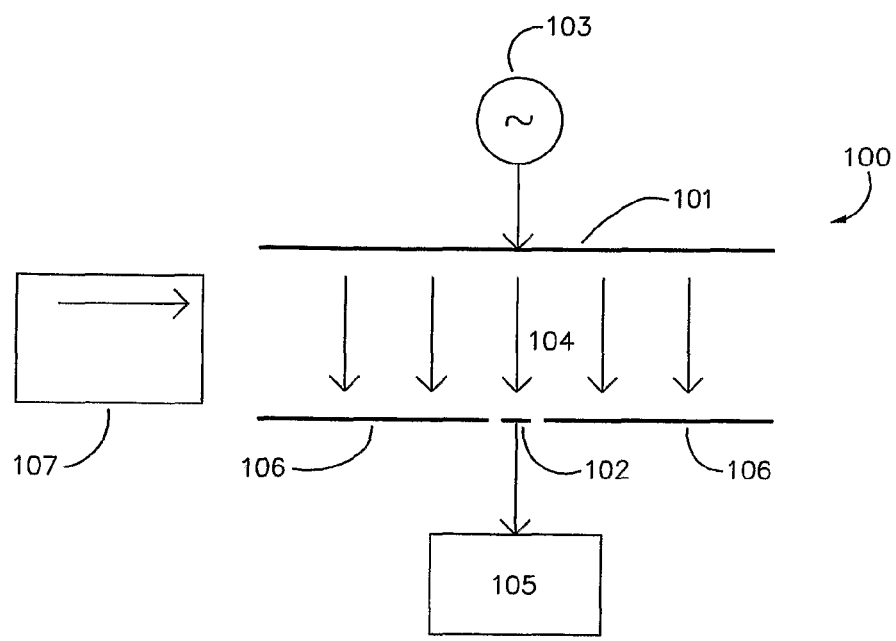
FIG. 1 illustrates, schematically, a detection apparatus.

FIG. 1 illustrates one form of detection apparatus 100. There is a first electrode 101, a second electrode 102, and in operation, a signal source 103 is provided causing a field 104 to be produced substantially between the first and the second electrodes. The resultant field is received and processed by logic 105. A third electrode 106 is provided proximate the second electrode and near the same potential, and causes the field 104 to be substantially linearised. When a product or material 107, for example a package, is passed through the field 104, its presence affects the field, as can be determined by the logic 105.

An example of a detection system is disclosed in U.S. Pat. No. 5,134,379, in which a product 107, for example, passing through the field 104 affects the substantially linearised field between the first and second electrodes. This, in turn, can be used to determine whether the contents of the package (for example when the package is full of its required contents) are to be considered acceptable, or rejected (for example when the package has missing or damaged contents). The detection system as disclosed in U.S. Pat. No. 5,134,379 utilises electrodes relatively fixed in position and a relatively linear field 104 between the electrodes.

Two Part Head

It has been realised by the present inventors that a detection system can be provided which is adapted to operate with moving components of production line equipment (for example robotic arms) and/or to be operable in a relatively temporary situation (for example a manual, portable or relocatable detection system).

Figure 2:
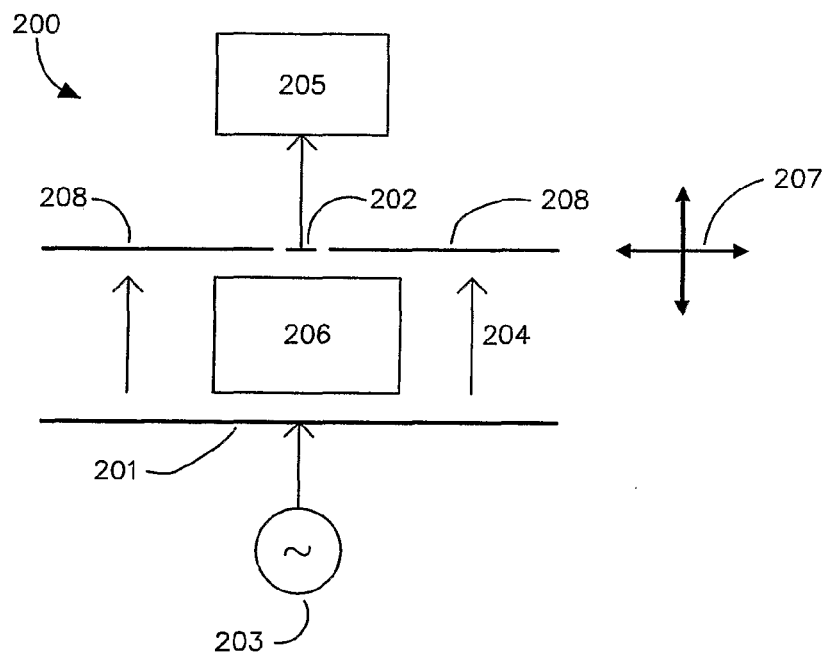
FIG. 2 provides an illustration of an aspect of invention, namely a detection system according to an embodiment of the present invention.

FIG. 2 illustrates a detection system 200 according to an embodiment of the present invention. There is a first electrode 201, a second electrode 202, a third electrode 208, a signal source 203, which in operation provides a substantially linearised field 204 use for detection, and logic 205 for determining the desired detection. When a product or material 206 is placed between the electrodes 201 and 202, the field 204 is affected, and this result is determined by logic 205. The field effect is representative of a characteristic of the product or material, and the logic may be biased to determine that characterisic(s). An example of a characteristic is as disclosed above.

In respect of the 'robot head' application, as disclosed herein, the applicable characteristics preferably include:
  Presence/Absence,
  Count,
  Fill Level,
  Orientation,
  Integrity,
  Shape and/or Profile,
  Conductivity, resistance, capacitance, and/or impedance and
  Other physical attributes as may be determined by the particular application and/or from time to time.

In accordance with the present invention the first electrode 201 is movable in any predetermined position 207. For example, the electrode may be movable in any one or any combination of directions X, Y and/or Z.

Furthermore, the second electrode may be moveable in any one or any combination of directions X, Y and/or Z. In a further alternative, both the first and the second electrodes may be moveable in any one or any combination of directions X, Y and/or Z.

The electrode(s) may also be rotatable or disposed in any orientation, relative to each other. The electrode(s) may also be displaced or moveable vertically and/or horizontally.

The first electrode 201 which acts to radiate the signal source may alternately act as a signal receiver, in which case the electrode 202 will act to radiate the signal source. The signal source is typically say 300 kHz and steady. In this way, the electrodes may swap their function, say, over say 500 times a second—i.e. swapping between FIGS. 7a and 7b, 500 times a second during which time the product or material to be detected only advances a few mm.

Robotic Application

The present invention enables a product or material to be inspected while in motion, such as when it is being moved using a robotic head. The benefits of such an approach compared with conventional inline (conveyed) package contents inspection are, at least:
  No additional production line length is required in typical installations.
  Multiple reject destinations (stacks or conveyor locations), depending on the characteristic fault detected
  The possibility of robotically correcting faulty product in some cases
  Detecting faulty product before placement, preventing further mess downstream that could require in major clean-up Example applications of the present invention are given in FIGS. 3 and 4. Preferably, the electrodes are arranged substantially parallel to each other during a detection operation. A product 306 can be inspected while being moved by arm 310 from conveyor or position 308 to conveyor or position 309. Arm 310 preferably has possible movement in any one or any combination of directions X, Y and/or Z as indicated by numeral 307. The product or material 306 is picked up by some suitable means 311, for example suction cups, and moved from position 308 to position 309 with the arm 310. The signal source 303 is applied to the first electrode 301 proximate the product or material 306. Typically the first electrode is under or beside product or material 306. As robot arm 310 moves the second electrode 302 and third electrode 312 proximate product or material 306, a substantially linear field (not shown) is created between the first electrode 301 and second electrode 302. Signal amplifiers 313 and signal processor 305 resolve the desired characteristics from information sensed by second electrode 302 as it traverses 307 the region nearby product or material 306. As can be understood, when the product or material 306 is in proximity of electrode 302, electrode 301 is also in proximity of electrode 302 (via the product or material 306) and a field (not shown) can be created between the electrodes, the result of which is that the product 306 can be scanned or the contents can be detected and determined as acceptable or rejected by logic 305. In a preferred embodiment, the field created between the electrodes 301 and 302 is a substantially linear field, and the electrodes are provided in the form as disclosed in U.S. Pat. No. 5,134,379. In this case, the product once placed at position 309 and over electrode 301, can be moved in a manner that detection can be made of a 'slice' of the product or material at any given instant in time. Thus, as the arm 310 moves 307 along position 308, detection of the whole of the product 306 can be made.

Figure 4:
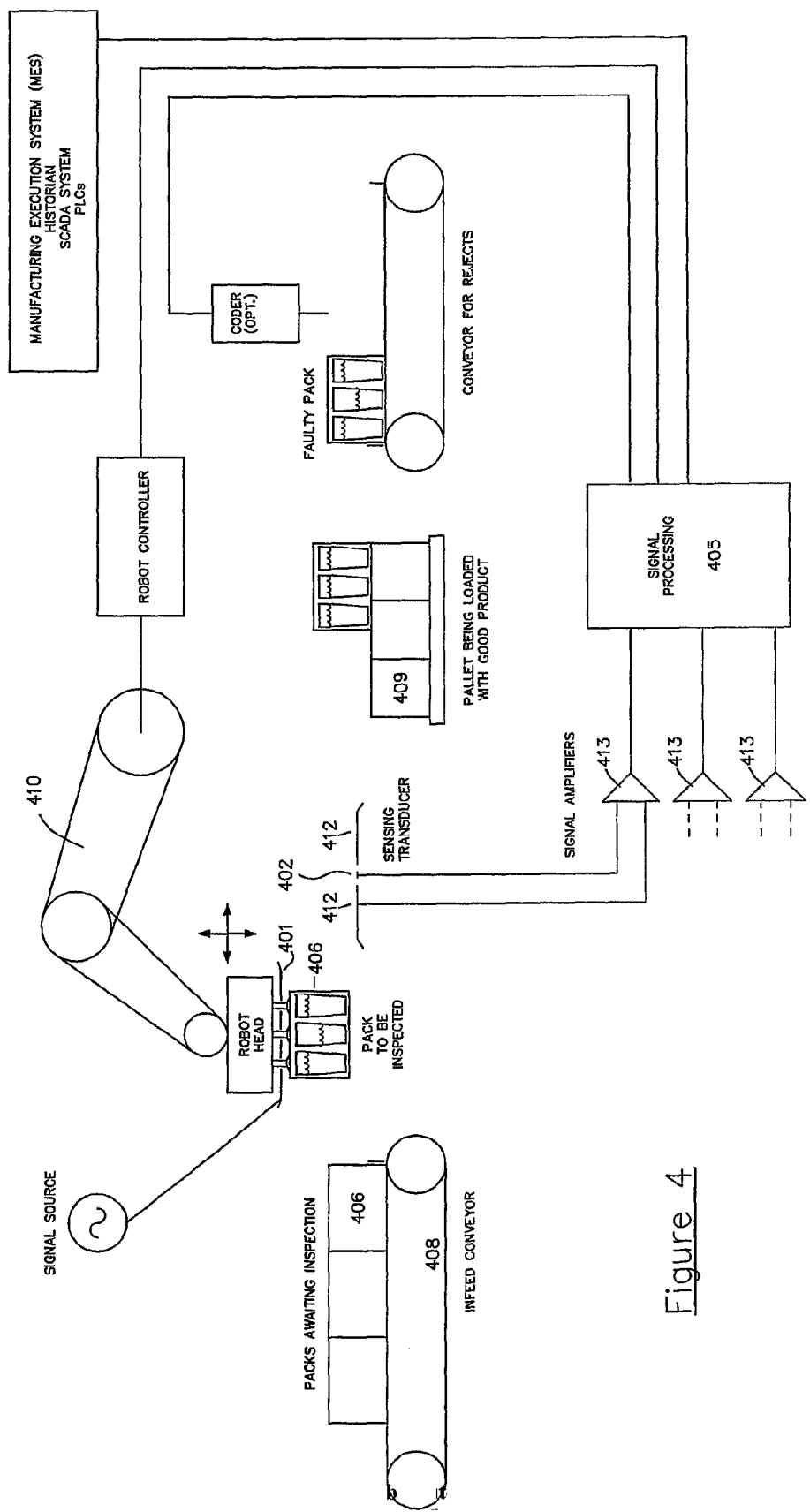
FIG. 4 illustrates another example application of the present invention.

FIG. 4 illustrates another example application of the present invention, in which a detection zone is created intermediate the movement of the product 406 from position 408 to position 409. Again, the detection zone may be created by the proximity of a first electrode 401 and a second electrode 402. The product 406 to be inspected can be placed in the detection zone, the detection field can be provided, and the resultant detection signal processed by logic 405 and associated amplifiers 413.

Figure 5:
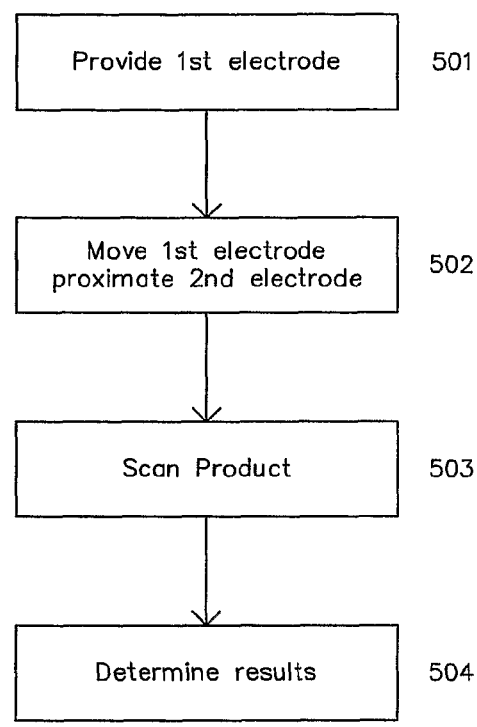
FIG. 5 illustrates a detection method according to an embodiment of the present invention.

At least two different configurations of electrode are possible—their advantages and salient features are described below:

FIG. 5 illustrates a detection method according to an embodiment of the present invention, in which a first electrode is provided 501. The first electrode is then moved into proximity with the second electrode 502. This enables a detection field to be created through which a product can be moved 503. Alternatively, the first electrode may be moved over the product, or the second electrode can be moved relatively to the first electrode. The results can be determined 504 and analysed and/or displayed in a suitable format as required. Depending on the results, actions may optionally be performed on the product such as moving the product further through the product line, rejecting the product, or correcting its fault.

Figure 6:
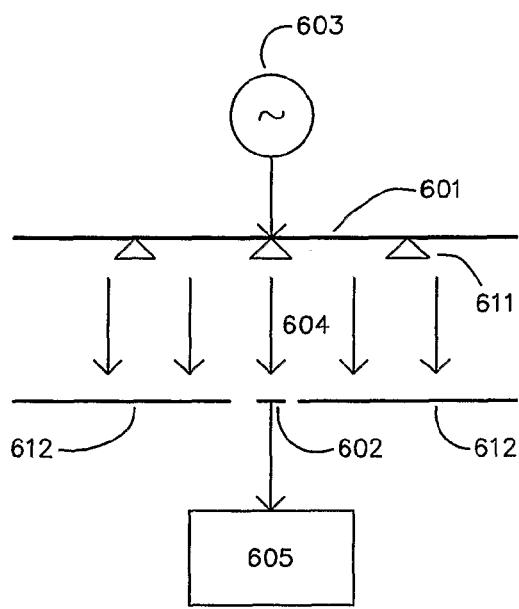
FIG. 6 illustrates electrode configuration according to the present invention.

FIG. 6 illustrates an embodiment of an electrode configuration suitable for use with the present invention. If the first electrode 601, supplied from signal source 603, is provided (optionally) with product holding or moving means 611 (such as suction cups or other suitable means depending on the product to be moved), then the product can be moved relative to a receiver 602. The second electrode 602 is preferably relatively small compared to the first electrode 601. There is also provided a third electrode 612 which acts to enable a relatively linear field 604 to be provided for detecting a 'slice' of the product at any one time. This is disclosed in more detail in U.S. Pat. No. 5,134,379.

FIGS. 7a to 7m Illustrate some examples, without limitation, of various electrode arrangements which may be adopted for use with the present invention. It is to be noted, that the examples are not an exhaustive detail of the various electrode arrangements, but are merely representative.

FIG. 7a illustrates an electrode arrangement in which there is provided an electrode 701 for receiving a signal and a transmitting electrode 702. 703 shows a third electrode which may be provided proximate the receiving electrode. Preferably, the third electrode 703 is at or near the same potential as electrode 702. Electrode 703 is shown in the various FIG. 7 arrangements, but, it is optionally provided in some arrangements.

The transmitting signals applied to the transmitting electrode in the various embodiments may be between a relatively low frequency and a relatively high frequency. For example, the frequency may between 80 to 300 kHz. The signals may be applied to each electrode alternatingly, that is the transmitting electrode may act as a receiving electrode, and vice versa.

Figure 3:
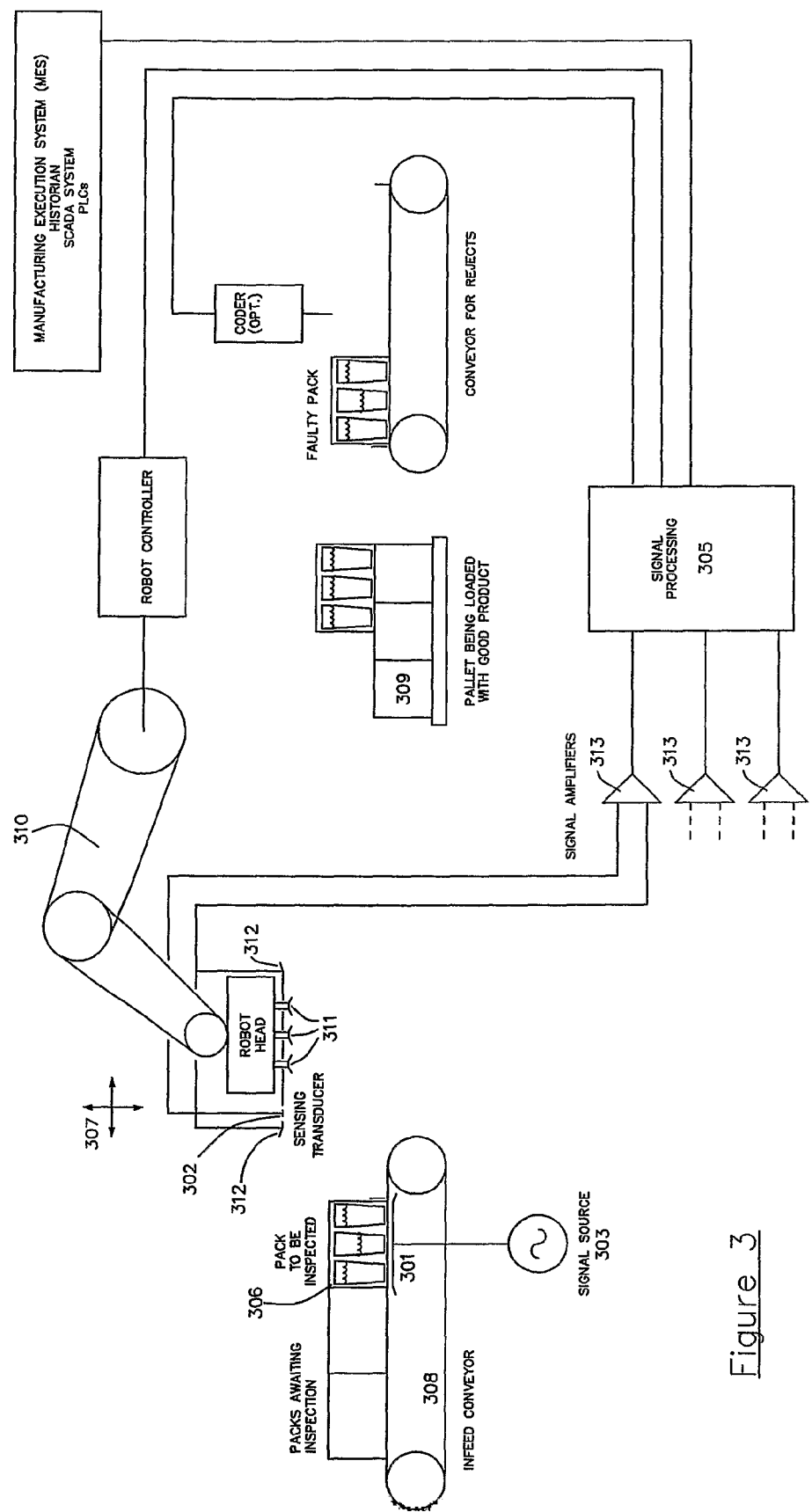
FIG. 3 illustrates an example application of the preset invention.

|  | "Top transmit" - see FIG. 4 | "Bottom Transmit" - see FIG. 3 |
| --- | --- | --- |
| Transmit Electrode location | Above product, mounted on robot head | Below Product, mounted below or beside infeed conveyor |
| Receive Electrode(s) location | Below product, mounted in fixed location in the transition path. | Above product, mounted on leading edge of robot head. |
| Scan time | Relatively late scan time, Scanned after pickup | Relatively early scan time, Scanned before pickup |
| Foil lid sensitivity | Works against gravity, Less foil lid sensitivity | Works with gravity, more foil lid sensitivity |
| Top section area | Compact top section approx same size as product | Top section larger than product |
| Closeness of sensing to product | Very close to product (at bottom) | Further from product unless conductive suction caps or similar device employed. |

The "foil lid sensitivity" refers to how easy it is to detect a whole missing foil lid on top of a tub of food for example. Higher foil lid sensitivity just means it Is relatively easy to determine that a lid is missing. Foil sensitivity could equally be referred to as "missing foil lid discrimination".

FIG. 7b illustrates a kinematic inversion of FIG. 7a.

FIG. 7b illustrates an arrangement similar to FIG. 7a, but that there is a larger transmitting electrode 702. Equally, a kinematic inversion of FIG. 7c can be provided in which the receiving electrode is enlarged.

FIG. 7d illustrates a movable part of a sensing head 705 and as herein disclosed and having a receiver electrode 701 and nearby linearising surface electrode 703. The transmitting electrode 702 is provided at or near a conveyor assembly 704. The conveyor 704 may be made from a relatively conducting medium, such as stainless steel slats or conductive rubber, in which case the conveyor itself may be used as the transmitter 702, assuming suitable signal coupling mechanism is provided.

FIG. 7e illustrates an arrangement in which the transmitting electrode 702 is movable 705 relative to the receiving electrode 701.

FIG. 7f illustrates an arrangement in which the transmit signal 702 is provided for reception by two receiving electrodes 701 and 706. This will enable various parts of a product to be detected, such as a 'top' and a 'bottom' of a product to be focused upon. Receiving electrode 701 will be more responsive to defects in the bottom of a product or material, while receiving electrode 706 will be more responsive to defects near the top of a product or material.

FIG. 7g illustrates another arrangement in which there is provided two receiving electrodes 701 and 706. Again this enables different parts of a product to be detected. Electrode 706 is useful for detecting the presence or absence of a component that substantially spans the distance between 706 and 702, such as a leaflet insert, promotional item, or sticky tape.

FIG. 7h illustrates a portable model in which the transmitter and/or the receiver may be moveable relative to one another. The transmitter may optionally be battery powered 707. In certain applications, a suitable synchronisation between transmitter and receiver may be required.

FIG. 7i illustrates an arrangement in which the transmitter electrode 702 in incorporated into or as a part of a conveyor roller 707. Equally, the inverse may be provided in which the receiver electrode is incorporated into the roller 707. A conveyor belt may also be optionally provided.

FIG. 7j illustrates a variation on FIG. 7i, in which the roller 707 is out of round (e.g. egg shaped) and the transmitter electrode 702 covers the surface of roller 707. As the roller turns, the transmitter signal will be provided closer to the receiver electrode, and then further away for the receiver electrode. This provides an alternating magnitude of detection of a product as it passes through the detection field 704.

FIG. 7k illustrates a detection zone in which the electrodes are provided at an angle to each other. Transmitting electrode 702 may be movable. Receiving electrodes 701. 706 and 708 may also be movable.

FIG. 7l illustrates an arrangement in which the receiver electrodes are position proximate the likely location of products 709. In this way, if one of the products is missing or defective, the receiver 701 and/or 706 can detect that situation.

FIG. 7m illustrates an extension of FIG. 7l, adding electrodes at half-pitch of the product where voids might be expected, which results in enhanced sensitivity to product defects.

Inspection Method

The inventors have also realised that during assessment of an individual product, each of these detection systems start by collecting data about the product (such as its weight during the time it is on the check-weighing conveyor, or an image in the case of x-ray or vision systems). The data collected is typically reduced using algorithm(s) to a single result, such as an estimate of the product's weight, the estimated count of items inside, a physical dimension, or a 'quality score' or 'figure of merit'. One or more thresholds and/or weights are used within the processing algorithm to reduce the relatively large amount of collected product data to a single result.

The reduced result or results determines the classification decision—whether to reject or accept the product. There may be circumstances in which the product is conditional accepted or rejected, which may require further processing and/or inspection. Because inspection equipment is generally not 100% accurate the following permutations are possible:

| True state of product | Good | Faulty | Good | Faulty |
|---|---|---|---|---|
| Classification Decision | Accept | Accept | Reject | Reject |
| Result | Good product reaches customer | Faulty product reaches customer | Good product in rejects bin of inspection equipment | Faulty product captured in rejects bin of inspection equipment |
| Human Interpretation | Content Customer | Unhappy Customer - potential complaint | Undesirable false rejects in reject bin. Extra rework. | Content Manufacturer |
| Feedback delay | N/A | Long | Short | Short |
| Cost to manufacturer | N/A | Reputation and Labour (complaints dept) | Labour (unnecessary), extra production time | Labour (necessary), extra production time |

By capturing the human interpretation as described above, the weights and thresholds can be 'fine tuned' leading to improved classification decisions in the future. This has the commercial benefit of reduced complaints and waste, enhanced reputation, and reduced labour both on the production line and in the complaints department.

Figure 8:
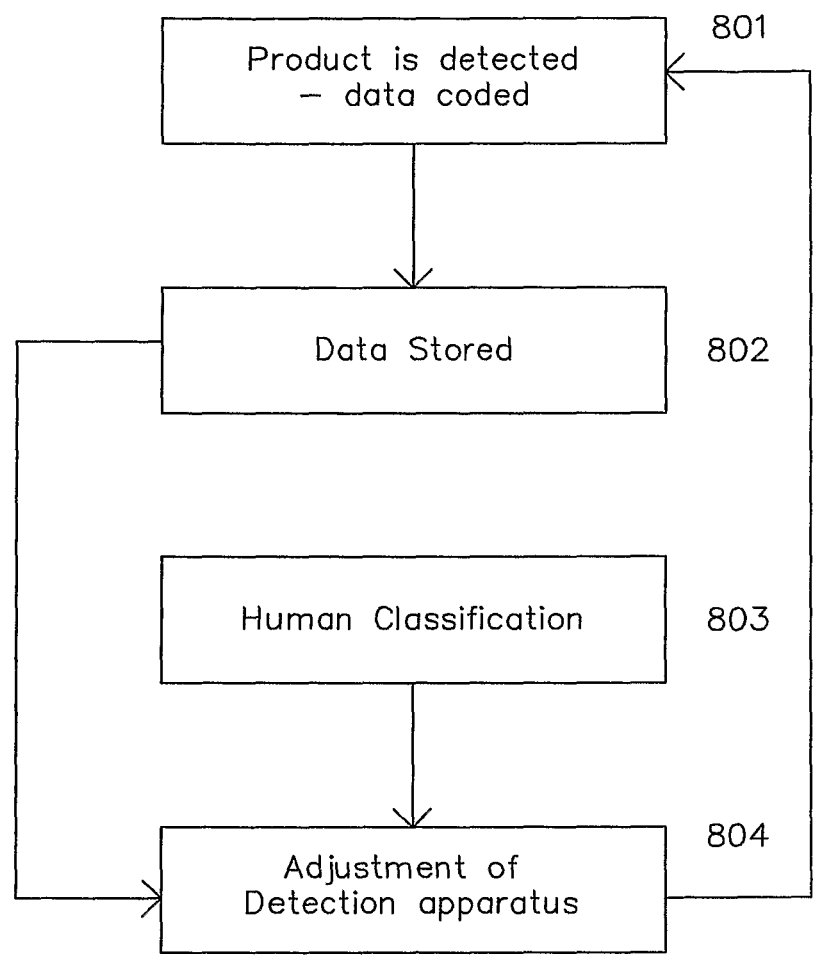
FIG. 8 illustrates an embodiment of another aspect of invention.

An embodiment of this aspect of invention is shown in FIG. 8. The present aspect of invention contemplates a feedback system to monitor and/or improve the operation of a detection apparatus. Initially the product is detected or scanned 801 by the detection apparatus, for example apparatus as herein disclosed or any other suitable apparatus. The data is recorded and/or stored 802 for later evaluation according to the present invention. Periodically and/or randomly, a product is inspected manually 803. The result of the manual inspection is compared with the result of the detection apparatus and the comparison is used to adjust (if necessary) to detection apparatus 804. This will lead to improved detection (again) at 801.

In a further example of the present invention, the result of the detection 801 is coded and stored 802 on the product itself. For example, the data that is coded can include, without limitation:

The final inspection result (overall quality score)
Intermediate results
Waveforms/pictures (raw data)
A serial number for future cross reference
Batch number and/or production time
Use-by date
Recipe information
Destination address data
A combination of the above The coded data may enhance traceability, statistics gathering, accuracy improvement, process improvement, and/or winning prize verification of the package that is coded.

The format of the coded data may include, without limitation:
A bar code (1D or 2D)—advantage of easy machine readability
Various permutations of conductive stripes, spaces, lengths, positions and/or thicknesses
A 'string' of digits or characters, such as a serial number, or inspection results. Possibly machine readable using a vision or RFID system
A waveform or image (raw)
A combination of the above The invention may include a means for capturing the human interpretation 803 manually or automatically and (optionally) a historical database for storing the original captured data, or a partial or fully derived result(s) from this data. There is also provided a means for analysing the human interpretation against the classification and a method and/or apparatus for adjusting the weights and thresholds 804. Optionally there is also provided a means for charting the improvement gains, and for reporting this data to a MES or SCADA system There are several methods available to code information onto each individual product. Commercially available systems include RFID, industrial laser markers, and industrial inkjet markers using standard visible ink or ultraviolet visible ink. A suitably conductive ink if used, has the benefit or being readable by the same detection apparatus described herein. It is also possible to provide laser etching of existing code information, the etching serving to modify the information in a manner that the modification becomes a code of Itself. The etching may not be discernable by the human eye, but readable by machine using some (any) suitable manner.

The system for capturing the human interpretation can be a manual or an automatic system, typically part of the inspection equipment itself. It can employ a combination of inputs such as a bar code reader or readers for rejects bin processing, but a web interface for remote QA processing. An example of a manual system might be a keyboard entry of the serial number together with a desired outcome (accept or reject). An example of an automatic system, assuming product has been coded with a machine readable marking such as a bar code—might include two or more bar code readers at the inspection equipment (reject bin processing). If an operator processing the rejects bins finds a pack should have been accepted (it is in fact good), they swipe it past the 'do not reject this pack again' bar code reader. If the pack is in fact faulty, they swipe it past the 'this pack is indeed faulty' bar code reader. Additional bar code readers could be used if there are multiple reject classifications, such as 'missing 1 item' or 'missing 2 items' or 'crushed contents'

For the case of actually faulty/classified as good (resulting in customer complaints from the field), it is more likely the complaints department or QA will be the receiver of the human interpretation information. For this case the bar code reader would not be as suited as perhaps a web interface page for entering the desired classification. The entry system can therefore be a hybrid of several input technologies.

To make use of the knowledge gained from the human classification information input described in the previous two paragraphs, it is generally necessary to review the original decision making process. The information entered in the human classification, such as serial number, is used to look up the data from a historian (archive).

Once the original information has been retrieved, and depending on the desired classification, that data is added either to the set of 'product signatures that should be accepted', or 'product signatures that should be rejected', or optionally another classification.

Periodically, the sets of signatures are analysed with the aim of optimising the weights and thresholds. The algorithm is thus fine tuned to obtain maximum discrimination between the signatures desired to be accepted and those desired to be rejected.

The discrimination statistics are also of interest, especially their trend over time. Such trend graphs are made available either via the inspection equipment interface, or remotely via a web server or similar device.

It should be noted that there is typically more than one fault classification, and this technique is therefore scalable to include several feedback mechanisms for different fault classifications.

The feedback capturing does not have to occur at the inspection machine. Feedback and desired results could alternatively be reported to an agent or the inspection equipment manufacturer, who fine tunes the algorithm(s) and deploys them back to the manufacturing sites. The advantage of this approach is the accuracy of a broader range of machines or software can be improved rather than just one production line inspection machine.

If an automated human interpretation capture system is used, such as RFID or bar code, this same system can be used to log the id of the human performing the interpretation. It can also be used to set the product to be inspected automatically.

The described system is well suited to being implemented in the form of a neural network. Neural networks are often 'trained' in this way using techniques such as back-propagation to adjust weights.

It is important to balance the feedback where possible. For instance, when a line operator processes the rejects bin, they should feed back information not only when an incorrect decision has been made (actually good/assessed as reject), but also when a correct decision has been made (actually faulty/assessed as reject). This ensures the most accurate overall discrimination.

Relatively Hard-to-Detect Target(s)

This aspect of invention relates to the problem of relatively reliably detecting what are considered to be 'hard-to-detect' items inside, outside and/or associated with packages. The items may be referred to as targets. One example is a target inside sealed packages. Another example of such a hard-to-detect target is a paper leaflet/brochure/pamphlet/label ("the target") inside, outside or associated with a carton containing a number of blister-packed medical tablets. In such a package it is considered important to verify with great accuracy that a target is present. It is also important to verify that the correct target is present, for example, it is considered a problem when an incorrect target is placed inside a carton, especially in the case of a medical carton.

A target may be anything that is desired to be detected. Preferably, the target is inside, outside or associated with a package. The target may form a wrapping around or be partially associated with another object.

Figure 9:
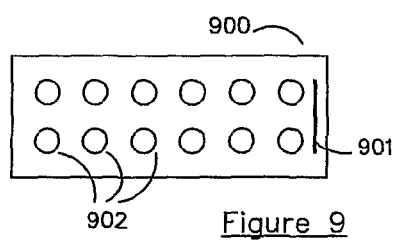
FIGS. 9 to 12 illustrate examples of packages containing targets to be detected.
Figure 13B:
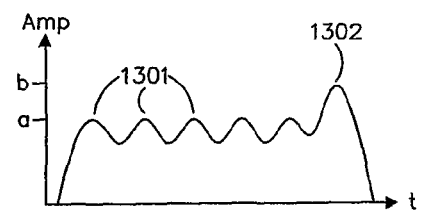
Figure 10:
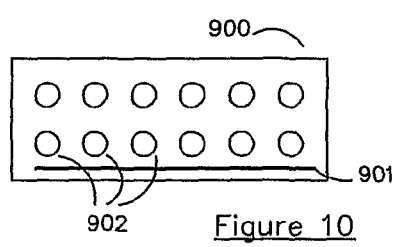
Figure 11:
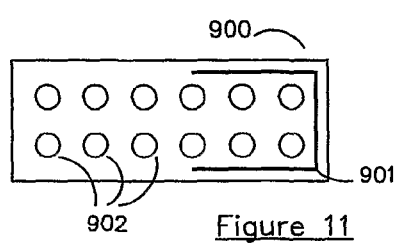
Figure 12:
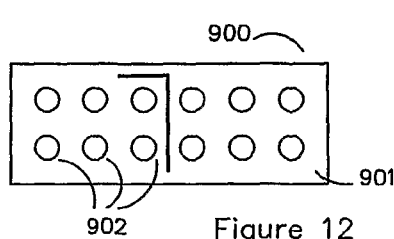

FIG. 9 illustrates an example of a package 900 containing a target 901 and a number of articles 902. The target may be positioned at one end of the package 900. FIG. 10 also illustrates an example of a package 900 containing a target 901 and a number of articles 902, but with the target positioned this time along one side of the package 900. FIG. 11 illustrates yet another example of a package 900 containing a target 901 and a number of articles 902, but with the target positioned around one end of the package 900. Alternatively, as shown in FIG. 12, the target may be positioned in the midst of the articles in the package. The inventors have realised that there are problems associated with the detection of a target in packages.

There are a number of embodiments of the present invention which are considered in singular or in any combination to be applicable to the detection of relatively hard to detect targets.

1. Scanning

U.S. Pat. No. 5,134,379, also by the applicant, describes apparatus that uses a capacitive technique to inspect inside sealed packs for the amount or presence of material. Equally, the disclosure of other inventive aspects in the present specification provides various embodiments considered useful in the detection of material(s) in packages.

It is important to note that a variety of scanning technologies may be used, such as that disclosed in U.S. Pat. No. 5,134,379, capacitive, x-ray, gamma, or other technologies as disclosed herein. The inventors have realised that one advantage of the arrangement as disclosed in U.S. Pat. No. 5,134,379 is that the arrangement of the receiving and transmitting electrodes provides a relatively narrow 'slice' of material in its detection zone. A further advantage realised by the inventors is that the equivalent impedance of the resolved 'slice' from the detection zone can be relatively large and thus the apparatus is relatively sensitive to relatively non-conductive, small and/or dry material.

Figure 13A:
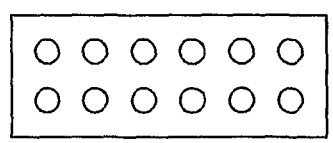
FIGS. 13 to 16 illustrate waveforms associated with the packages containing targets as shown in FIGS. 9 to 12, FIG. 17 to 20 illustrate schematically various embodiments related to package scanning.
Figure 13A:
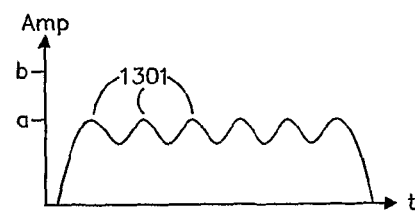

An example of detection waveforms is shown in FIGS. 13a to 16, resultant from a package moving through a detection zone. The waveforms shown in FIGS. 13a to 16 correspond to packages whose ordinary and hard-to-detect components have similar effect on the resultant waveform, such that both components can be visually distilled. FIG. 13a illustrates schematically a scan of a package (of FIG. 9) but without a target. Each of the contents 902 of the package 900 of FIG. 9 is represented as a peak 1301, each peak having an approximate amplitude approximately 'a'. In FIG. 9, there are six 'rows' of contents 902, and thus as the package 900 moves through the detection zone, there are six corresponding peaks 1301 in FIG. 13a. FIG. 13b illustrates a scan of the package of FIG. 9, but now containing the target 901. It can be seen that the target 901 has caused an elevated peak 1302 having an amplitude 'b'. In this manner, it can be understood that the presence or absence of a target 901 in a package 900 (of FIG. 9) can be correlated with a resulting waveform from a scan as represented in either FIG. 13b or FIG. 13a, respectively.

Figure 14:
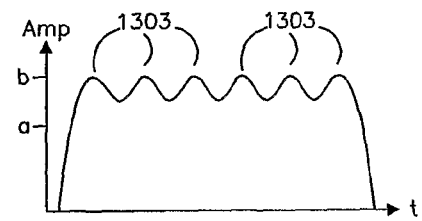

Likewise, FIG. 14 illustrates schematically the presence of a target 901 as illustrated in FIG. 10. As the target 901 is present substantially along the length of one side of the package 900, the resultant waveform of FIG. 14 shows six peaks 1303, each representing the presence of the package contents 902 and the target 901 at an elevated peak of amplitude 'b'.

Figure 15:
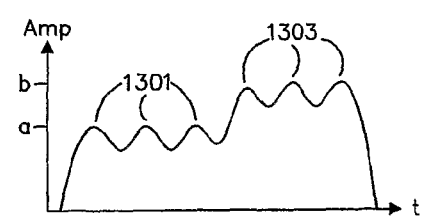

FIG. 15 illustrates schematically the presence of a target 901 as illustrated in FIG. 11. It can be seen in FIG. 11 that the target is proximate half the contents 902, and thus the resultant waveform illustrated in FIG. 15 shows a waveform having peaks 1301 having an amplitude 'a' for the portion of the package away from the target, and elevated peaks 1303 corresponding to the location of the target.

Figure 16:
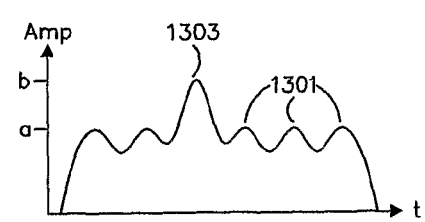

FIG. 16 illustrates schematically the presence of a target 901 as illustrated in FIG. 12. The target 901 resides in the midst of the contents 902, and thus FIG. 16 illustrates a peak 1303 having an elevated amplitude 'b' corresponding to the location of the target 901 in FIG. 12.

If a package 900 is scanned by a detection system according to an aspect of the present invention, and is sensed not to have a target, for example, the result waveform will be similar to FIG. 13a, and the system can be designed or calibrated to reject to package, or take other appropriate steps to notify of the defect (lack of target 901 in package 900). Although the embodiments refer to waveforms, a signal resultant from the detection process may be analysed or otherwise processed by appropriate logic to provide an output as required by the particular application. In other words, the desired output may provide a signal in a production line to 'reject' or 'accept' a particular batch or package(s).

A further aspect of invention has come about due to the realisation by the inventors that in, certain circumstances, it is possible to encounter some sensitivity, such as, in addition to detecting desired components for example the ordinary contents of the pack, some undesired components may also be seen in the waveforms emanating from the detection process. This sensitivity may typically include additional signals resulting from the package itself, moisture, or signals due to additional components such as additional brochures or unwanted material or components. The presence of the additional signals may also be determined from the resultant detection waveforms or output signals from the detection process to verify and/or indicate the presence, absence, placement location, integrity, or number of the target or targets. Equally, the waveforms or output of the detection process may be analysed using neural networks or various forms of AI (artificial intelligence) to compare detection scans against a 'library' of predetermined results, thus enabling a decision to be made (manually or automatically) as to whether the package(s) or acceptable or to be rejected.

The reliability of the detection of the target may be improved by controlling a number of aspects of the target, such as proximity, placement and/or orientation of the target, and/or conducting multiple scans of the package to take account of various possible orientations of a package(s).

2. Target Doping

In another embodiment of the present invention, the target may be modified and/or enhanced. For example, the target may be doped with conductive ink or some other material which can be sensed by the apparatus and/or method(s) of the present invention(s). In essence, the target may be modified, doped or enhanced with a material or chemical which provides some form of 'field interference', and thus may be detectable in accordance with the present invention.

The 'strength' of doping required depends on the ordinary contents of the package and the amount of contrast desired between the ordinary contents and the target(s). For example, typical impedance range for 'antistatic' grade sticky tape is 100 kohms per square to 1 gigohm per square.

In a further form of the present invention, a barcode or other indicia may be provided on or in association with the target. The shape or form of the indicia may be formed so as to provide a predetermined output in the detection process. For example, the indicia may be a barcode. The barcode may be formed of material which provides field interference and thus a resultant detection. If the barcode is scanned, the 'bars' of the code may be 'read', in which case the 'code' of the barcode may be determined. This may be particularly advantageous in a production line, especially if different targets are associated with different packages. The barcode and/or package may be 'read' and thus it can be determined if the correct target has been associated with the correct package. Alternatively, the barcode or indicia may determine which algorithm is applied to the information 'read'.

If the target is doped, determining a useful conductivity (range) of the target may be done experimentally, depending on the particular application of the present invention. The process followed depends on whether the substrate and/or ink forming the indicia is being modified.

If the substrate is being modified, multiple layers of a sheet of known conductivity may be stacked to determine the approximate required conductivity for the proposed target substrate.

Equally, one or a plurality indicia and/or inks (for example) may be used in association with the target. The indicia and/or inks may provide characteristic(s) suitable for use with the present invention(s). An example of suitable inks may comprise conductive polymer or metal based dispersive compounds, for example Agfa® Orgacon® EL-P 3000 series or EL-P 4000 series inks, or inks based on carbon or silver. In this case, the 'reading' of the indicia may provide a pattern of conductive inks, thus providing a corresponding pattern of field interferences and thus 'readings' associated with the indicia. The inks may be applied using inkjet technology. An advantage of this is that the indicia can be 'read' by the detector. If the target is conveyed in a predetermined orientation, and the electrodes are arranged appropriately, the target may be 'bar coded' to give a signature and/ or indicia which is uniquely dependent on the spacing of the bars, for example. Such a bar code is simplified, with a conductive bar of fixed spacing at two ends of the target, plus one or more bars in between to uniquely charactense the target. Furthermore, the conductivity of one or more bars may be provided in a predetermined manner with or without retaining a substantially consistent spacing.

In another embodiment, the conductive ink may be applied to a tamper evident seal. If the seal is broken, the conductivity 'path' is interrupted or changed, and this interruption or change may be 'read' by the detection machine. For example, the impedance 'read' of a seal that has been tampered with may be relatively different than a seal which has not been tampered with.

In one form, methods of controlling the conductivity of the target include, but are not limited to,
- Using a conductive printing ink, with or without changes to the graphics,
- Using two or more different conductivity inks, may provide a characteristic contrast;
- Modifying the conductivity by use of a laser or other suitable etching;
- Modifying the substrate (conductive or antistatic, paper or plastic)
- Physically attaching the target to a conductive marker (for instance, wrapping the hard-to-detect target in a conductive bag)
- Providing indicia of varying length (the length providing a relative form of coding)

3. Sensing Characteristic

In another aspect of invention, the inventors have realised that the sensing for a characteristic between two points may be used advantageously. For example, if it was required to sense the presence of a material (for example sticky tape) on a package, as the package passes through the detection zone, and using, for example, the apparatus as disclosed in any one of any combination of FIGS. 7f, 7g, 7l, 7l and/or 7m, the characteristic of the sticky tape can be measured. Again, for example, with reference to FIG. 7f or 7g, a characteristic of the sticky tape may be measured between electrodes 702 and 706. Equally turning to FIG. 7l, a characteristic may be measured between electrodes 701 and 706. Furthermore, turning to FIG. 7L again, a measurement may be made between electrodes 702 and 701. The presence or absence of the material, such as sticky tape, will provide an effect on the signal received by electrode 701. That is the sticky tape will, to some extent, provide an at least partial conductive path for the signal transmitted by electrode 702.

The reliability of the detection of the target may be enhanced by controlling the following aspects of the target, such as with out limitation, the electrical conductivity of the target or a portion thereof.

It has been found that there exists an optimum range for the electrical conductivity of a target, and it is thus possible to reliably detect both the
- Characteristic(s) of the target, and
- Characteristic(s) of the ordinary contents within the pack.
  - The present invention has advantageously been found not to substantially interfere with normal metal detection. Thus detection of target and metal detection can be carried out substantially without interference with one another.

If the electrical conductivity of the target is too high, it will dominate the signal due to the characteristic(s) of the ordinary components within the pack.

If the electrical conductivity of the target is too low, it will be dominated by the signal due to the characteristics of the ordinary contents within the pack. Sticky tapes typically designated 'Antistatic' are generally suitable, such as '40' series tape manufactured by 3M.

A number of examples are provided in FIGS. 17a to 20. In these figures the target patterns 1704, 1705 may reside on the outermost surface of the outer package, within the outermost package structure (e.g. patterned metallised film in a plastic sandwich), on the inside surface of the outermost package, on the outside/within/on the inside an internal leaflet, brochure, pouch or wrapper, or on the outside surface of an internal product, for example a biscuit or confectionery bar, or on a tamper seal of a bottle.

Figure 17A:
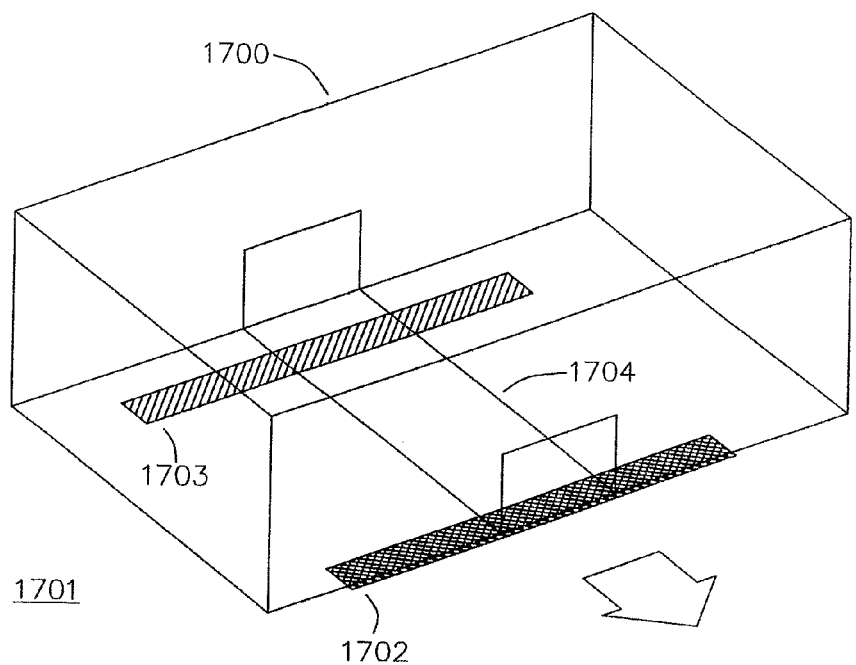

FIG. 17a illustrates schematically a package 1700 passing through a detection zone 1701 and as indicated by the arrow. Transmitting electrode 1702 and receiving electrode 1703 are provided in the detection zone 1701. In this embodiment the system is provided to detect the presence or absence of sticky tape 1704. The sticky tape has a characteristic, preferably at least slightly conductive, relative to the package and/or the package contents so as to enable a signal to pass between the electrodes 1702 and 1703. Upon receipt of the signal via tape. 1704, the presence of the tape can be confirmed.

Figure 17B:
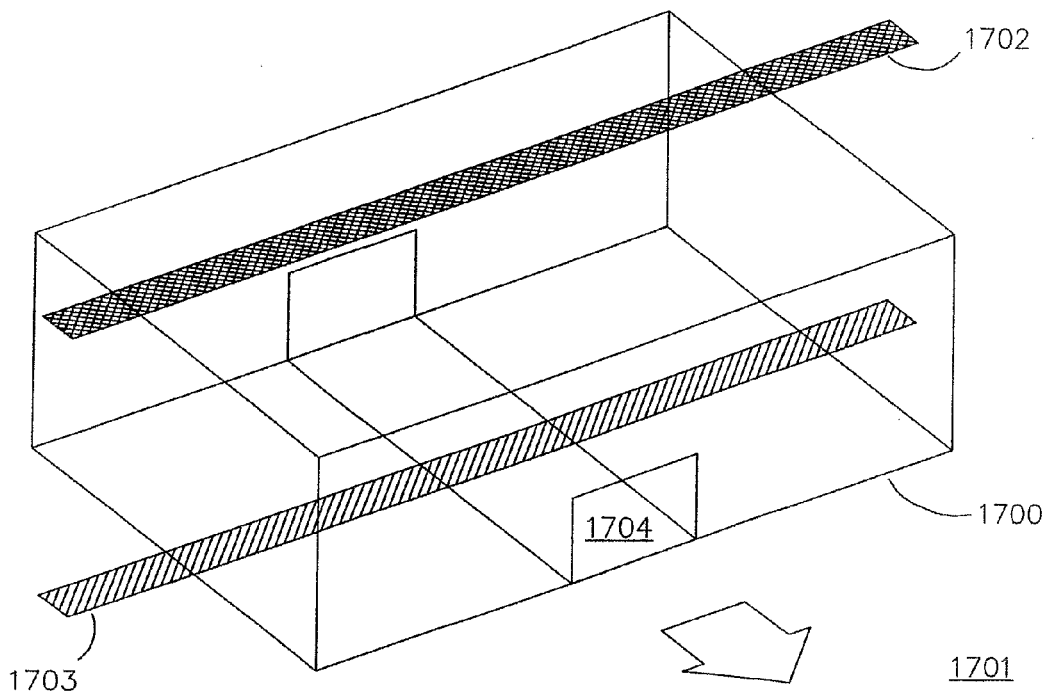

FIG. 17b illustrates a similar arrangement, but with the electrodes 1702 and 1703 disposed opposite each other.

Figure 18:
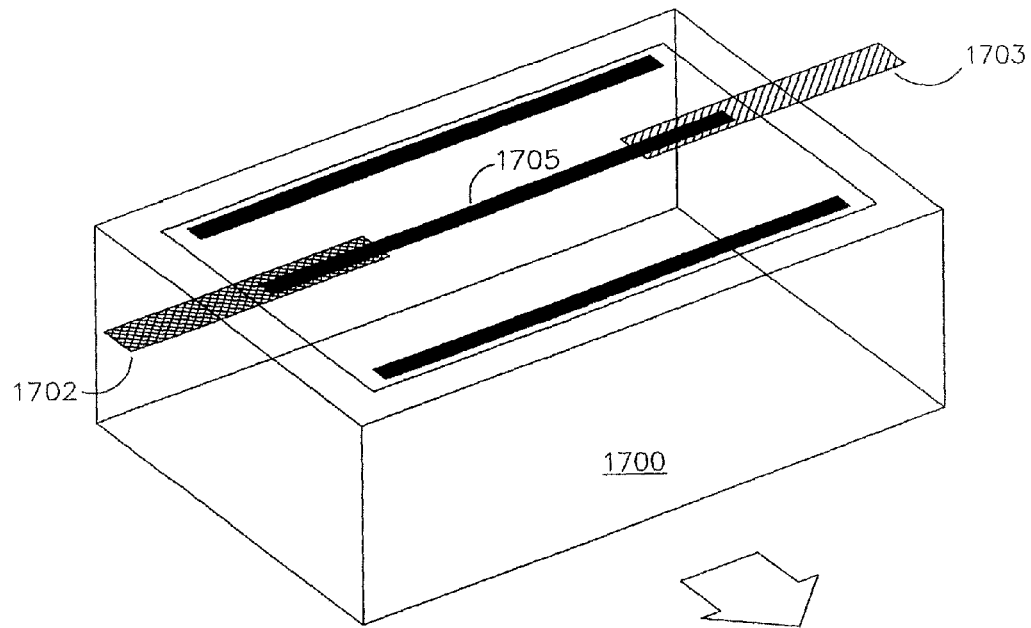

FIG. 18 illustrates schematically the sensing one or more conductive stripe(s) 1705. This is provided by the stripe (having a characteristic, preferably conductive) relative to the package 1700, and can be detected as it passes electrodes 1702 and 1703. Upon a stripe being sensed between the electrodes, the characteristic can be confirmed. Furthermore the position of the centre stripe 1705 relative to the outer stripes 1705 can be used to verify the correct target is present. Additional stripes may be added, in a similar manner, to increase the amount of information encoded. Any of the electrodes may be any size, and may take into account package skewness. Preferably the transmitting electrode is made larger to allow the overall apparatus to be more tolerant of skewness.

Figure 19A:
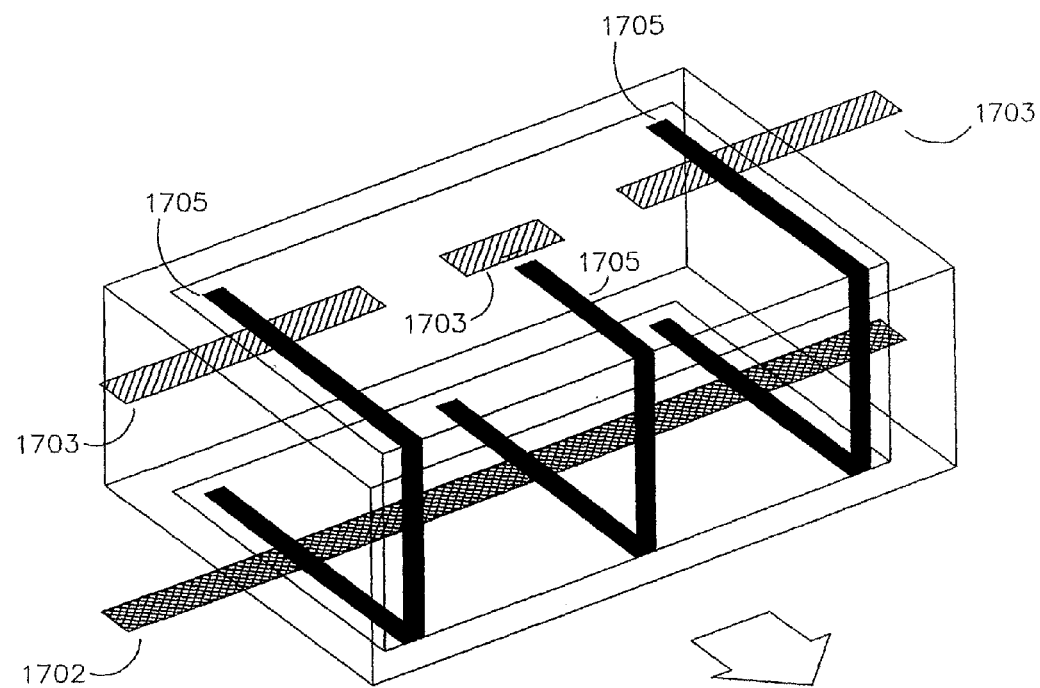

Further to this, FIG. 19*a* illustrates schematically a manner in which the positioning of the electrodes and/or the indicia may be used to provide a 'code' indicative of the package being detected, or the correct identity and placement of an internal leaflet or brochure. For example, the stripes 1705 may be provided and offset with respect to one another. As shown in FIG. 19*a*, the two outer stripes 1705 are proximate the electrodes 1702 and 1703. The stripes conduct the transmitted signal around the internal contents such that they can be 'read' by electrodes 1703 without significant interference from the signal due to the ordinary internal contents of the package. The orientation, extent, positioning and/or conductivity of the stripes and their respective electrodes may provide a 'coding' such as a digital 1 or 0s coding indicating conducting, not conducting, respectively over a certain time period. Alternatively an analog quantity may be encoded, based on the relative timing detected for centre stripe 1705 relative to outer stripes 1705. The digital or analog encoded information-may be used, for example, to identify the exact target present. Additional stripes and respective electrodes 1703 may be added in the same manner to increase the amount of information encoded.

Figure 19B:
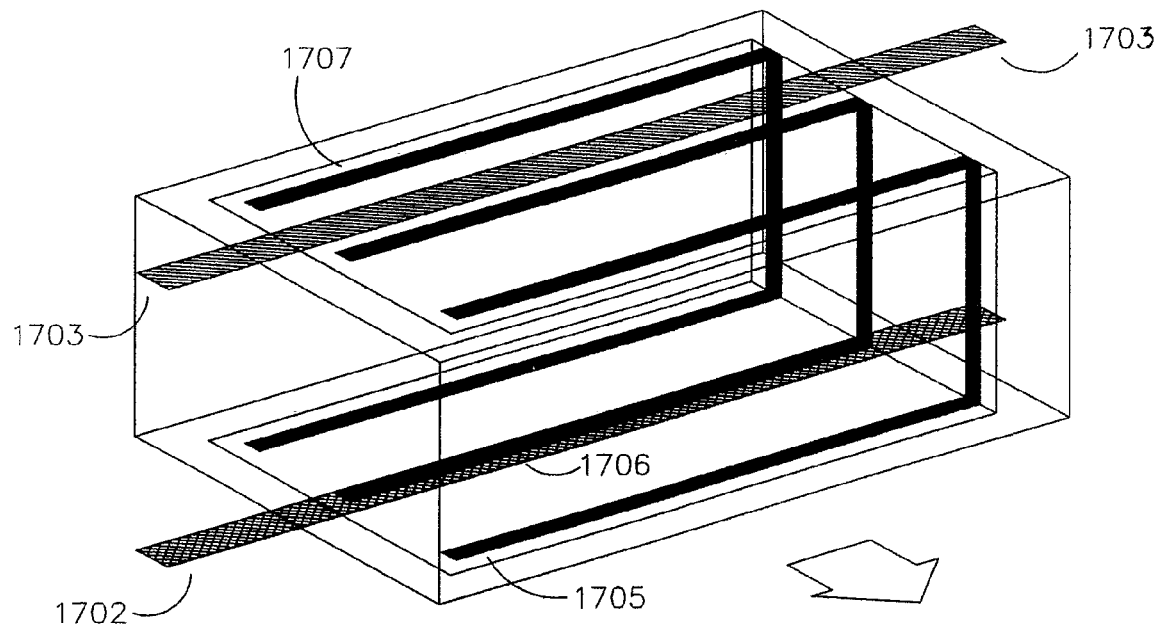

FIG. 19*b* illustrates a similar arrangement to that of FIG. 19*a*, however the orientation and/or positioning of the electrodes 1702 and 1703 provide a 'coding' in respect of the distance or spacing between, for example stripes 1705 and 1706, and stripes 1706 and 1707, or any combination thereof.

Figure 19C:
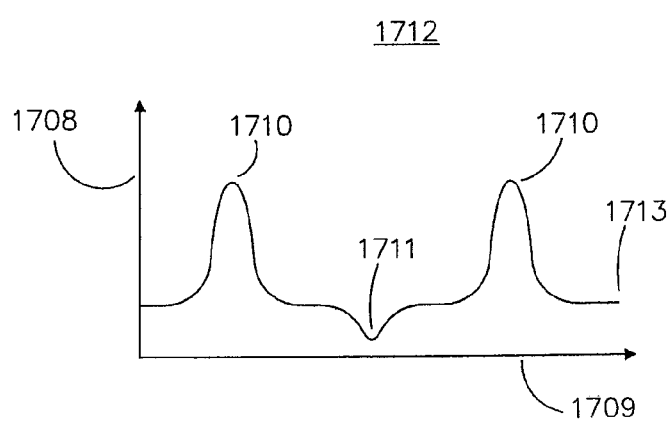

FIG. 19*c* illustrates one possible waveform 1713 created by passing a package as illustrated in FIG. 19*b* through the detection zone. Axis 1708 is the phase sensitive detector output after minimal processing, while axis 1709 represents time or alternatively displacement as the package passes through the detector. The outer stripes 1705 and 1707 in FIG. 19*b* have similar relatively conductive properties, and give rise to peak responses 1710 in FIG. 19*c*. Middle stripe 1706 in FIG. 19*b* is much less conductive than the outer stripes, by approximately two orders of magnitude, such that its self capacitance cannot be ignored. Relatively less conductive stripe 1706 gives rise to peak response 1711 in FIG. 19*c*. For reasons of clarity, no ordinary contents or their corresponding response is shown in FIG. 19*c*.

Figure 19D:
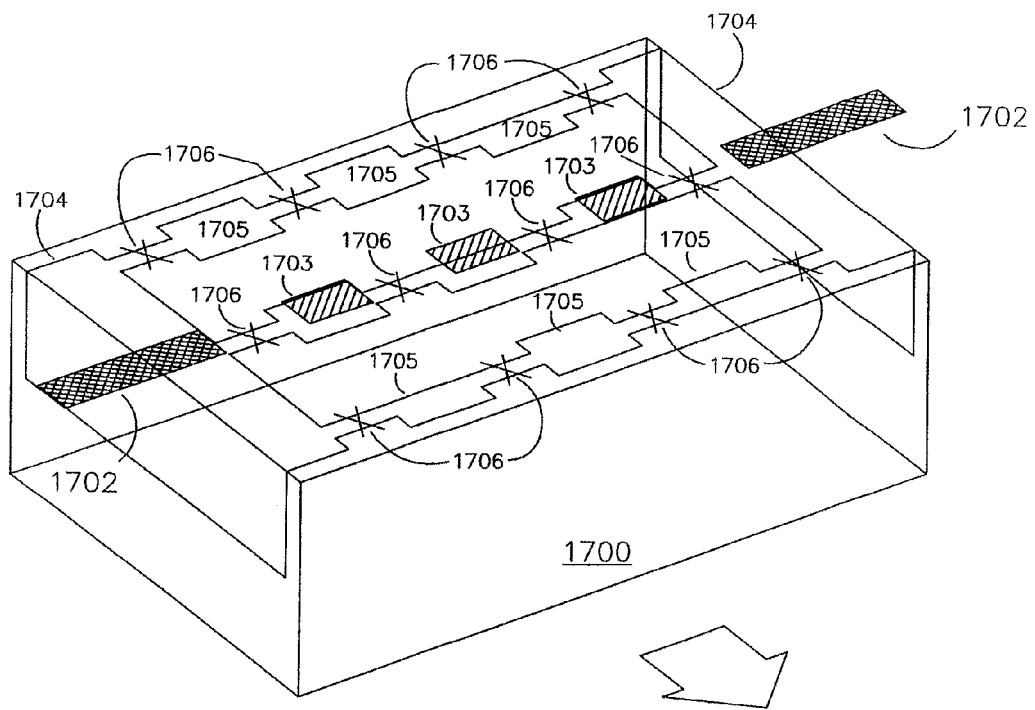

FIG. 19*d* illustrates a related embodiment designed to substantially increase the encoded information density. Signals from transmitting electrodes 1702 are received by large 'signal collectors' 1704. Collectors 1704 may extend beyond one face in order to collect signal in the most effective manner. In such cases transmitting electrodes 1702 may be disposed in a suitably effective orientation relative to collectors 1704. Signals from collectors 1704 pass along relatively conducting stripes to relatively conductive 'islands' 1705. The width and offset (in the direction of travel) of the islands are varied in order to encode information, and this information is detected by respective receiving electrodes 1703. To change the encoded information, for example record inspection results onto the package 1700, the pattern may be modified by 'breaking' the relatively conductive stripes at two or more sites 1706 nearby one or more 'islands' 1705. Such an action effectively makes one or more 'islands' substantially invisible to the receiving electrodes 1703 and related detection process.

One practical example of 'breaking' is by using an industrial laser marker with suitable calibration to break at the required sites. Such a process may also be applied to any of the other embodiments described by FIGS. 17 through 20.

Figure 20:
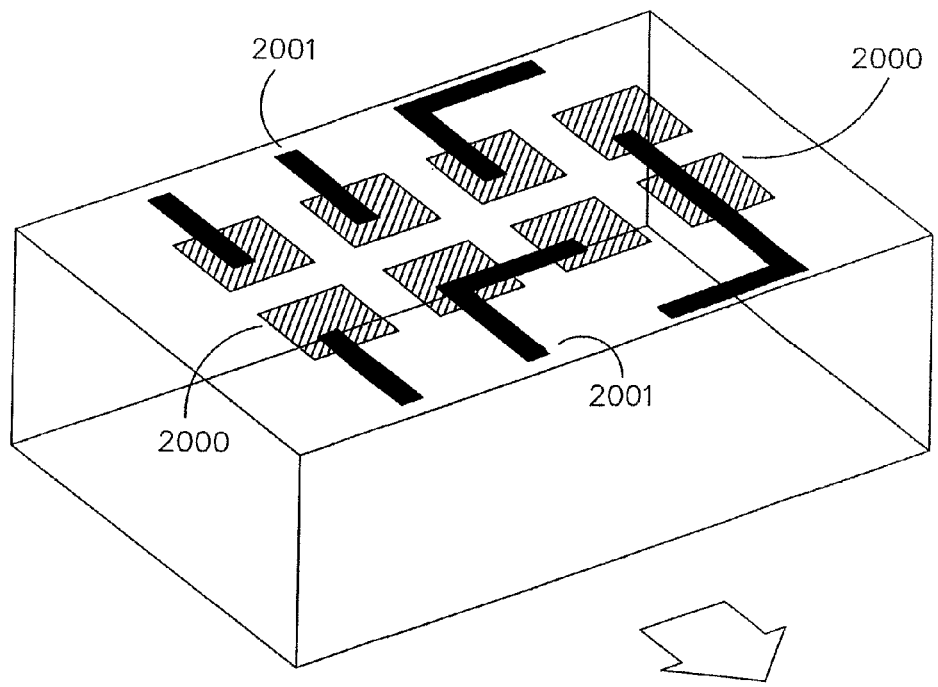

FIG. 20 illustrates an embodiment further to FIGS. 19*a*, 19*b*, 19*c* and 19*d* in which the arrangement of electrodes 2000 and/or indicia 2001 provides a conductive 'data matrix' arrangement. In this embodiment, any one or more of the electrodes are activated as transmitting electrodes and any other or more of the electrodes are activated as receiving electrodes. The electrode functions are switched in sequence until all data matrix elements proximate the electrodes have been evaluated. The sequence of signals received, as determined by the positioning of the indicia will provide the resultant 'coding' for detection.

4. Characteristic Contrast

The present inventors have found that what may be referred to as a 'contrast' of characteristics (such as conductivity) may provide enhanced detection of a characteristic and/or target.

Three examples methods of characteristic contrast are:

a. Dual Phase Detector

The signal generated by a detection when a pack is scanned may be provided to two phase detectors. One phase detector is tuned to be most responsive to the target (generally a more conductive path), while the other phase detector is tuned to be most responsive to the ordinary contents.

Figure 21:
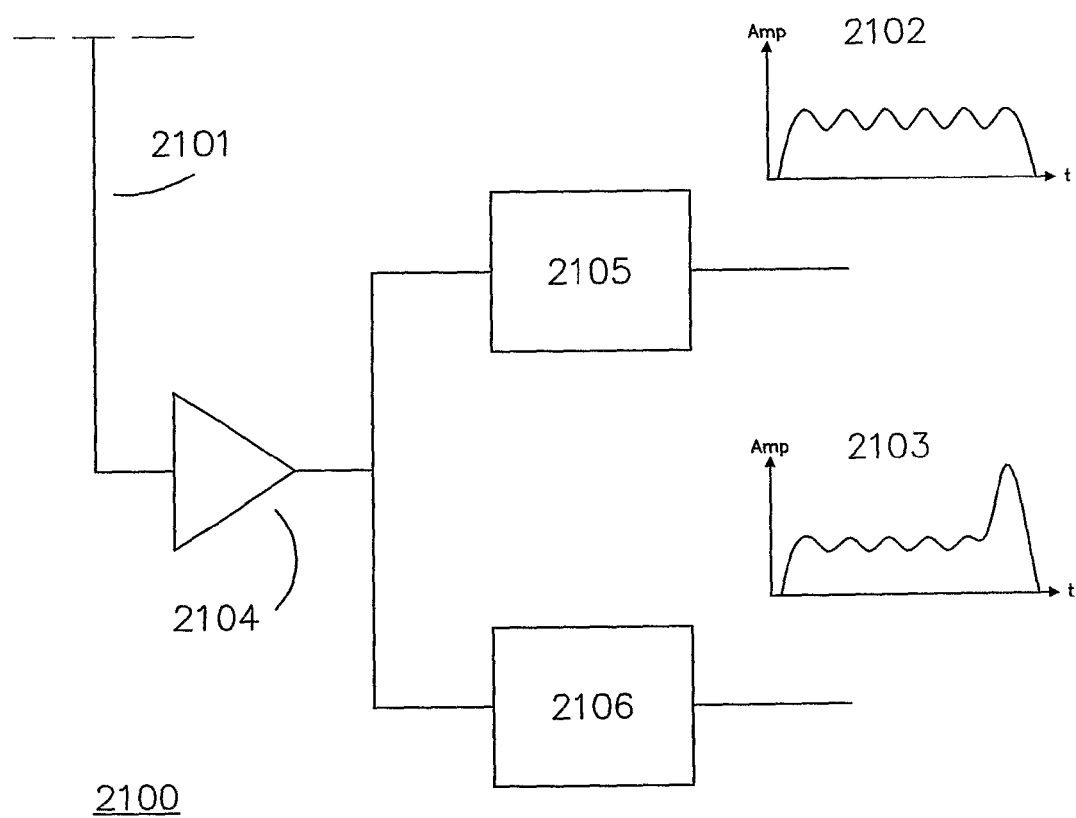
FIG. 21 illustrates schematically an embodiment of a signal receiving and processing circuit associated with an aspect of invention.

FIG. 21 illustrates schematically a signal receiving and processing circuit, in which a received signal is provided by electrode 2101, amplified by amplifier 2104 and provided to comparative circuits and/or logic 2105 and 2106. Circuit and/or logic 2105 is relatively sensitive to the ordinary contents of a package, and circuit and/or logic 2106 is relatively sensitive to the target. If a package is scanned by the circuit, for example that described by FIG. 9, then waveform 2102 responsive to the ordinary contents is produced by circuits and/or logic 2105, while waveform 2103 responsive to the target is produced by circuits and/or logic 2106. The circuits and/or logic of FIG. 21 may be replaced with another form of suitable detecting circuits and/or logic.

b. Subtraction

The detection may be designed to provide two output signals, again one output being biased toward a target or desired characteristic, and the other output not being so biased. One signal may be subtracted from the other, thus providing a resultant measure of a differential signal, which may be processed and/or enhanced to provide a predetermined level of sensitivity.

c. Comparison

In a somewhat similar manner to subtraction, a comparison of signals may be used to amplify differences, and lead to predetermined sensitivity of detection.

5. PCIS Bottle Inspection

This embodiment describes apparatus and method for inspecting products for quality defects. One typical application is inspecting the fill level of liquids or tablets in bottles as they pass down a conveyor. FIGS. 22 to 30 assist in the description of this embodiment.

What is described herein can be generalised to determining the dimensional extent of relatively conducting material (optionally) inside a relatively insulating container.

The term "fill extent" will be used to describe the extent of conducting material regardless of whether it is liquid, solid or loose solids (e.g. tablets).

5.1.1 First PCIS Embodiment

This embodiment disclosed comprises apparatus and method(s).

The apparatus is based on that described in patent U.S. Pat. No. 5,134,379 by same authors. In U.S. Pat. No. 5,134,379 the transmitting and receiving electrodes are opposite each other. In this embodiment, the electrodes are perpendicular to each other. The advantage of the technique described here is a greatly reduced installation requirement, as the equipment can be installed 'over the top' of an existing production line.

Figure 22A:
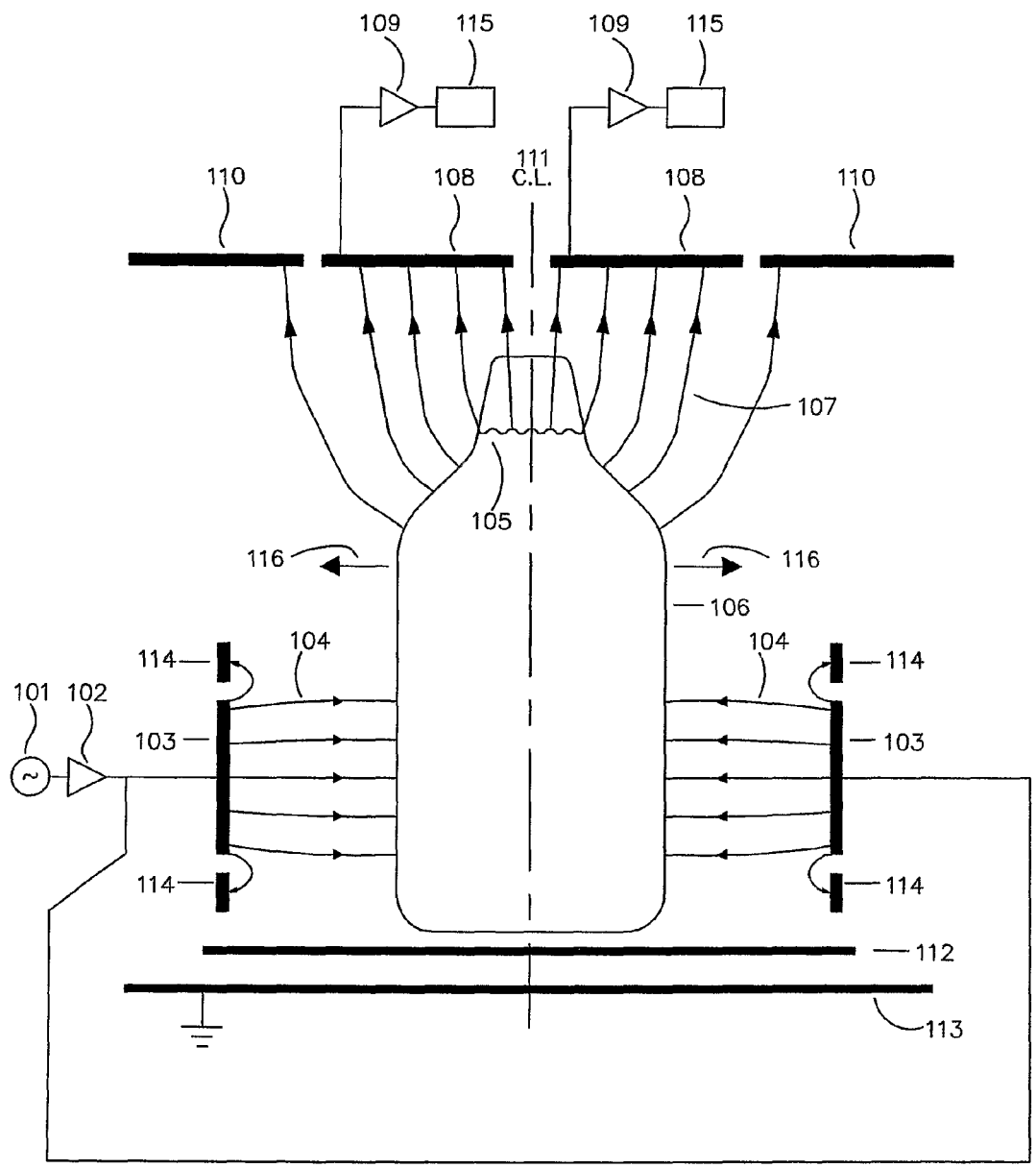
FIGS. 22a, 22b and 23 illustrate embodiments of invention for detecting fill or product level in one or more containers.
Figure 22B:
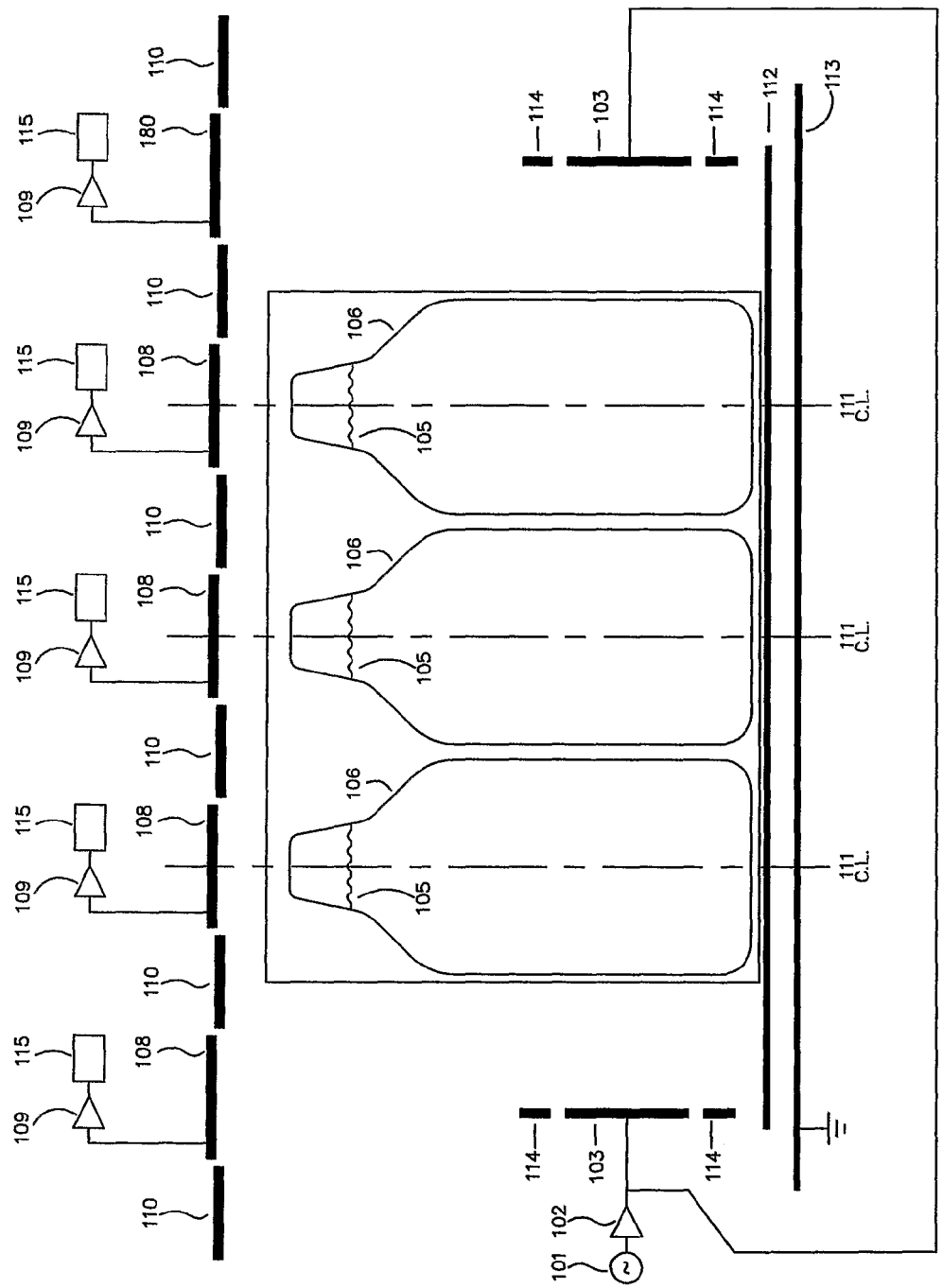

The proposed arrangement is shown in FIGS. 22*a* (view along conveyor), 23 (plan view) for the nominal case, and FIG. 22*b* for a multiple container case. In these figures the product being inspected is being moved by conveyor 112 running above conveyor bed 113.

Figure 24:
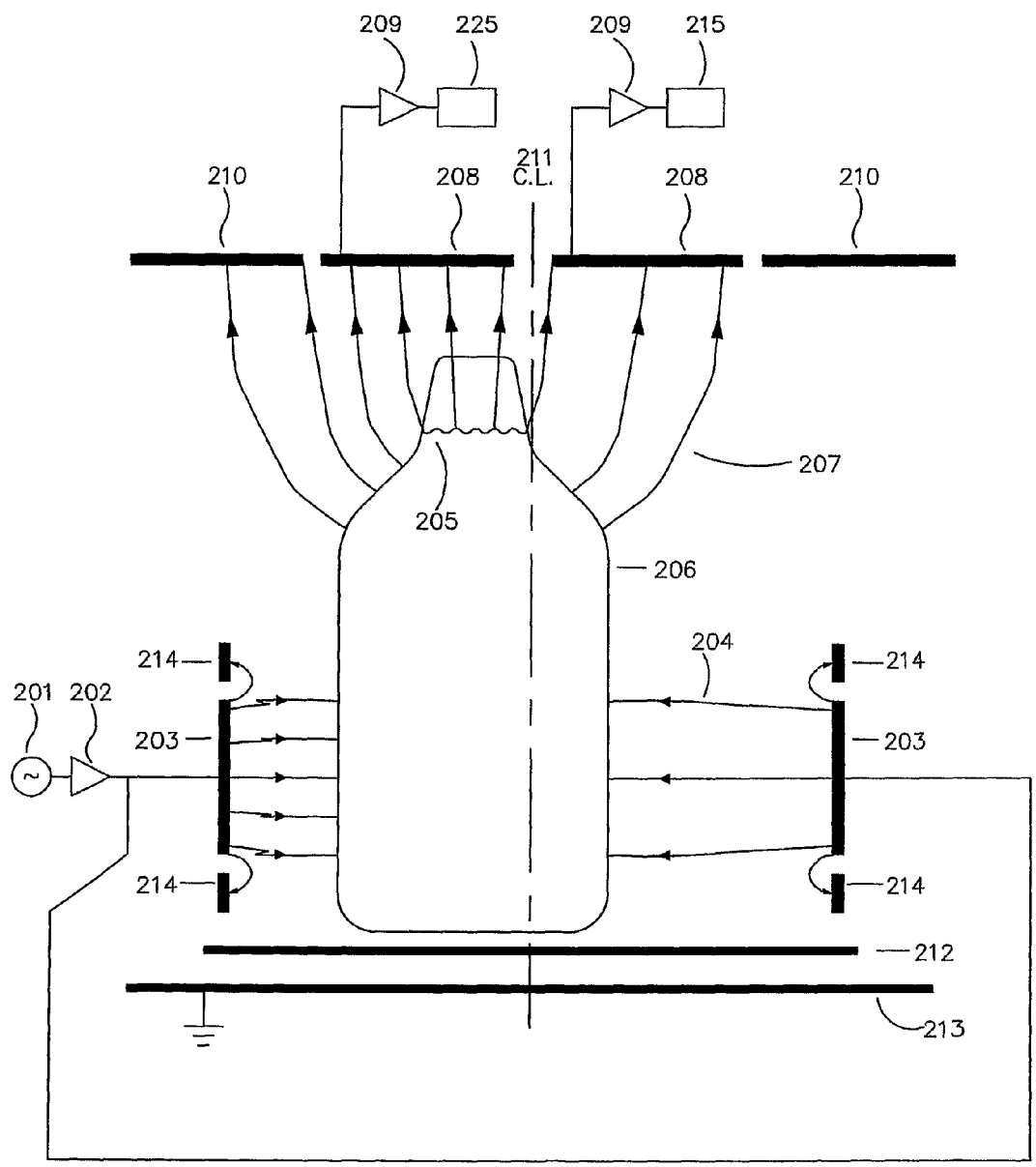
FIG. 24 shows the laterally displaced case (view along conveyor) of another embodiment of invention.

FIG. 24 shows the laterally displaced case (view along conveyor)

The processing method employed here is substantially different from U.S. Pat. No. 5,134,379.

The apparatus is described by the following sections:

5.1.1 Means for Generating and Amplifying a Sinusoidal Transmitting Signal

A means for generating a suitable transmitting signal is described in U.S. Pat. No. 5,134,379 and this may be used in conjunction with the present invention. The frequency of the generated sinusoid is typically in the range 10 to 10000 kHz, typically 300 kHz. The sinusoidal source is item 101 in FIGS. 22*a*, 22*b* and 23. The sinusoid is amplified by amplifier 102 in FIGS. 22*a*, 22*b* and 23. The voltage of the amplified sinusoid is typically in the range 3 to 300 volts peak. Typically it is 20 volts peak.

The driving impedance of the amplifier 102 is relatively low so that build-up of product, glue, dust, stickers etc on the transmitting electrodes does not substantially affect the amount of transmitted signal.

5.1.2 Means for Coupling the Transmitting Signal to the Product Being Inspected

Figure 23:
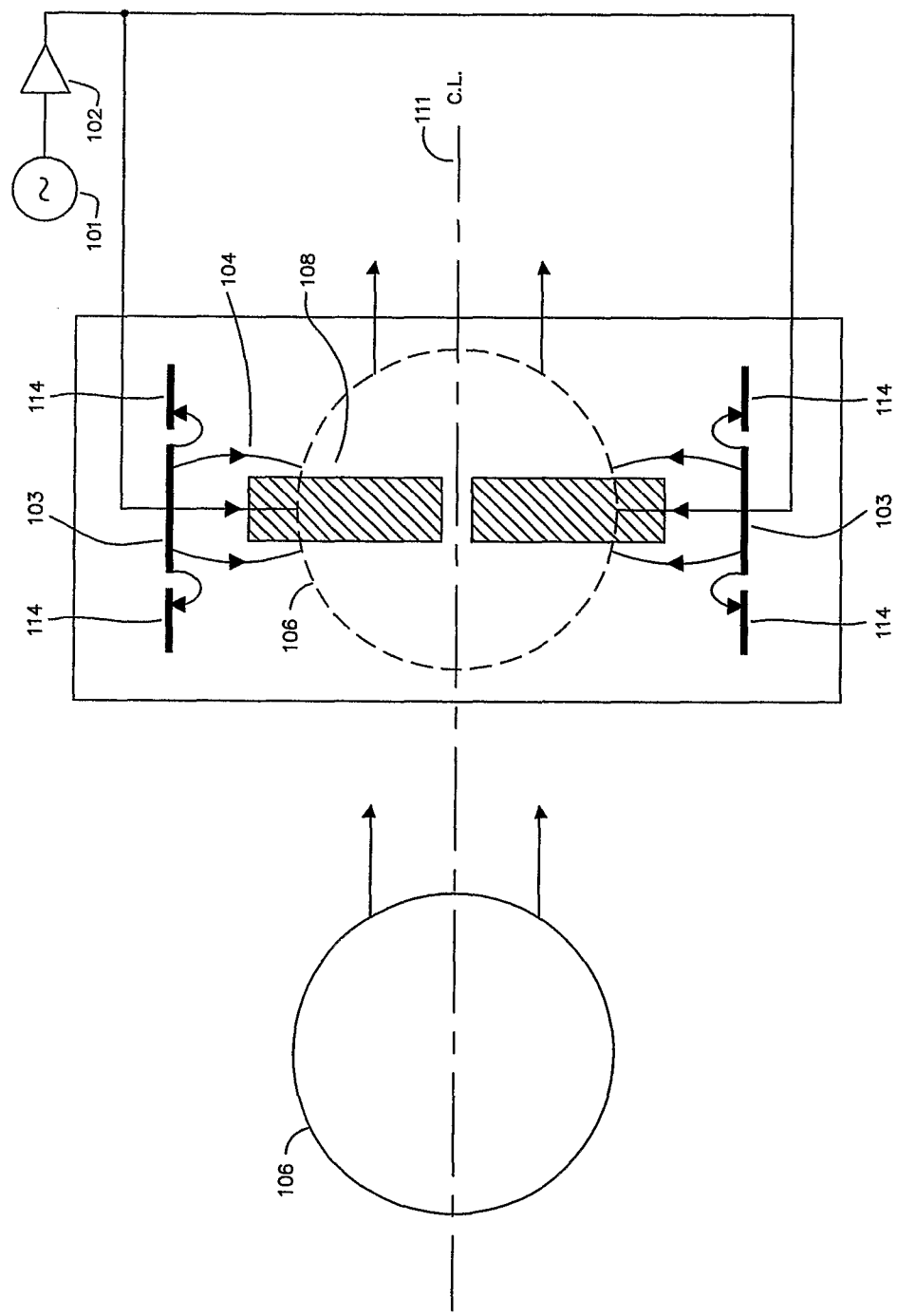

A preferred apparatus for coupling the transmitting signal to the product is described in FIGS. 22*a*, 22*b* and 23. The apparatus comprises of two transmitting electrodes 103 located either side of the product being inspected. The product being inspected passes nominally through the centre 111 of the two transmitting electrodes.

The transmitting electrodes 103 are preferably spaced apart from the product as this reduces the sensitivity to lateral displacement of the product. The typical separation of the transmitting electrodes is preferably in the range of 1 to 4 times the individual product diameter.

The transmitting electrodes may preferably be surrounded by earthed linearising surfaces 114 to help reduce fringing field 104. It is to be noted that the linearising surface, may in other embodiments/applications, not be earthed.

In FIG. 22*b*, the electrodes 108 may be arranged proximate the centre line (CL) of each container being detected. This enables each electrode, and its associated circuitry to provide detection for each container proximate the electrode, substantially independently of other containers and/or electrodes. A linearising surface 110 may also provided intermediate the electrodes 108.

5.1.3 Signal Coupling within the Product

Referring to FIGS. 22*a*, 22*b* and 23, the transmitted signal is coupled internally through the product being inspected 106.

If the product being inspected is a liquid then the surface 105 of the contained liquid acts like an equipotential surface. The field lines (flux) therefore depart the top liquid surface largely perpendicular to the liquid surface.

If the product being inspected is dry (such as tablets) then the coupling takes place by a mixture of conductive and capacitive mechanisms.

Either way the transmitted signal is present in a diminished strength 107 at the top of the product near the receiving electrodes 108.

5.1.4 Means for Coupling the Signal Exiting the Product to the Receiving Electrodes The signal leaving the top of the product 105 is coupled to the receiving electrodes 108 via the flux lines 107. Alternatively, there may be only one electrode 108 provided. The receiving electrode(s) 108 are driven to nearly the same potential as the intermediate linearising surface(s) 110 by the amplifiers 109 similar to that described in U.S. Pat. No. 5,134, 379. Combined with the surrounding linearising surface 110, this has the effect of linearising the received field lines (flux) 107.

In FIG. 22*b*, it is shown that the receiving electrodes 108 may be displaced, preferably vertically, relative to the linearising surface 110. This displacement serves to localise the field received by the electrode 108. Electrodes 120, which may be provided along side the 'normal path' of the containers 106, are adapted to receive signals in the event that the container(s) 106 are displaced or skewed away from electrodes 108.

The displacement of any electrode relative to the linearising surface may be provided in any of the embodiments disclosed herein. The displacement serves to define the effective operational resolution of the electrode, alleviate signal Interference from nearby electrodes, adjacent objects/product and/or sources of noise, etc. The displacement may be applied to any or any combination of transmitting and/or receiving electrode(s).

5.1.5 Means for Amplifying the Received Signals

The transmitted signal detected on the receiving electrodes 108 is amplified 109 similar to that described in U.S. Pat. No. 5,134,379.

5.1.6 Means for Processing the Received Signal(s)

Each amplified signal is compared with the original transmitting signal using a signal processing block 115. Signal processing block 115 comprises a phase sensitive detector and, in its simplest form, means for thresholding or peak detection. The height of the peak is mostly dependent on the fill extent of the product.

It may also dependent on any or any combination of:
- the lateral displacement of the product relative to the transmitting electrodes 103,
- the presence of transient conductors such as steel pins in the conveyor belt 112,
- the electrical permittivity of the product being inspected 106. This is generally constant.
- Bottle shape, including side wall distortion
- Cap and/or seal integrity Other suitable circuitry may be used depending on the type of signal that is required to be received.

5.1.7 Means for Compensating for Lateral Movement of the Product

Means for compensating for lateral displacement of the product are shown in FIGS. 22*a*, 22*b*, 23 and 24.

The lateral displacement 116 of the inspected product relative to the transmitting electrodes 103 has some effect on the amount of signal coupled into the product, and therefore the signal at the receiving electrodes 108.

The two split receiving electrodes 108 are independently processed by blocks 115 using the method described in the previous section.

For lateral displacements 116, the coupled signal (and therefore the received signal) Is at minimum when the product is central 111 between the transmitting electrodes 103. The signal increases with lateral displacement 116.

The preferred method for reducing the effect of lateral displacement 116 is to use two adjacent receiving electrodes 108, each nominally receiving half of the signal 107 exiting the product being inspected when the product is in the centre 111 of the transmitting electrodes 103.

If the product being inspected is displaced laterally, as shown in FIG. 24, this will result in an increased peak signal received by one electrode 208, and a reduced peak signal received by the other electrode 208.

Figure 25:
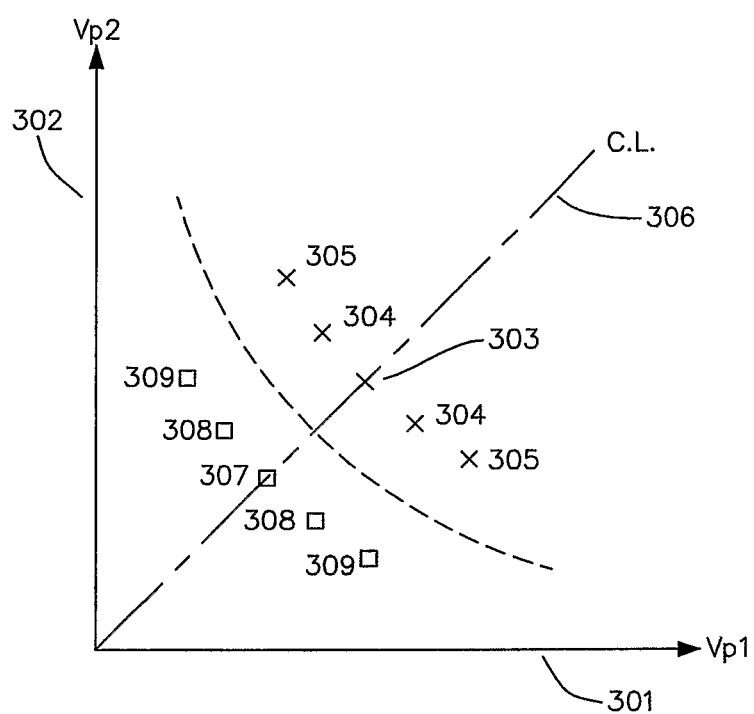
FIG. 25 illustrates an example method of compensating for lateral displacement of product.

FIG. 25 shows graphically the results obtained as the product is laterally displaced. FIG. 25 plots one peak reading from block 115 against the reading from block 115 corresponding to the other receiving electrode 108. These peak readings are represented by axis Vp1 (301) and Vp2 (302).

For a product with correct, nominal fill extent, marker 303 represents the results for the product passing centrally between the transmitting electrodes 103. Markers 304 represent the product being laterally displaced slightly either side of centre. Markers 305 represent the product being laterally displaced substantially either side of centre.

For an underfilled product, marker 307 represents the results for the product passing centrally between the transmitting electrodes 103. Markers 308 represent the underfilled product being laterally displaced slightly either side of centre. Markers 309 represent the underfilled product being laterally displaced substantially either side of centre.

From FIG. 25 it can be seen that, for small lateral displacements, the sample points follow the approximate trajectory of a rectangular hyperbola (Vp2=a/Np1), where 'a' is a constant depending on the fill extent and other constants. The other constants arise from the level of applied signal, and geometric considerations such as the transmitting electrode separation, distance from the receiving electrodes to the product being inspected, distance between the nominal product surface 105 and receiving electrodes 108.

Figure 26:
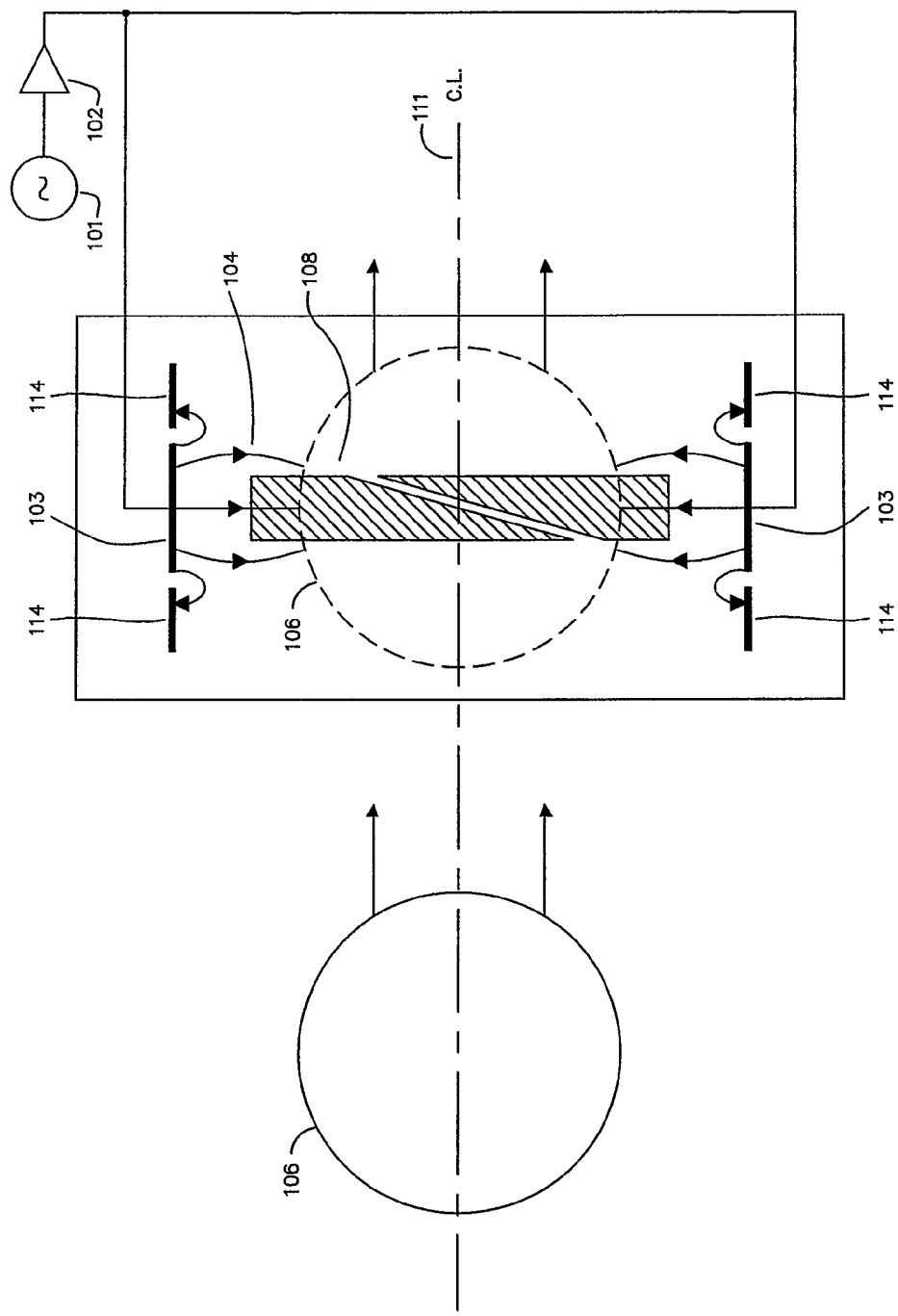
FIG. 26 illustrates an embodiment of invention for detecting fill or product level in a container, having tapered receiving electrodes.

FIG. 26 shows a variation on FIG. 23 where the receiving electrodes 108 have been tapered. The effect of this is to reduce the sensitivity to lateral displacement at the peak output stage of the signal processing block.

Figure 27:
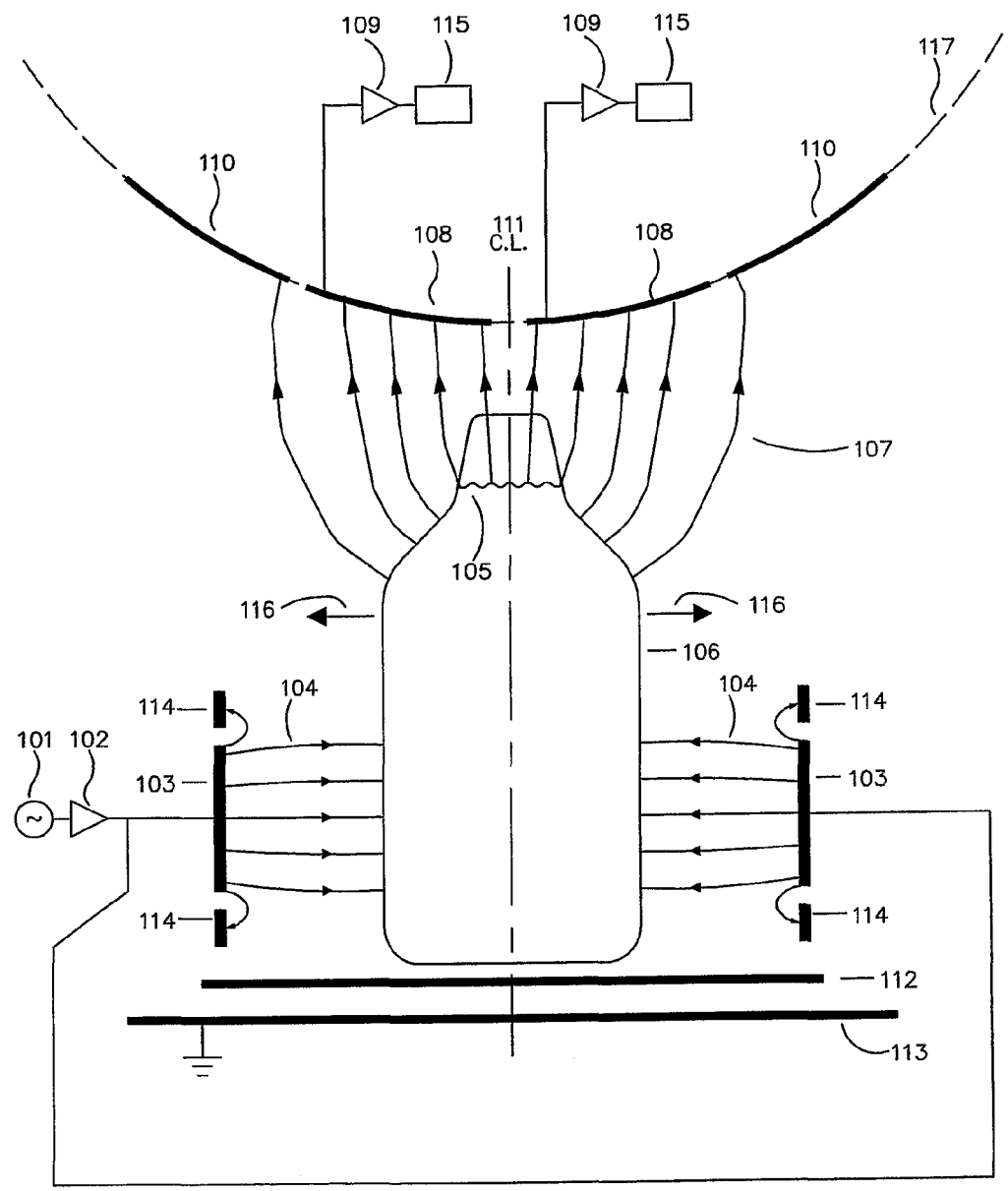
FIG. 27 shows an embodiment of invention for detecting fill or product level in a container, having curved or relatively non-linear receiving electrodes.

FIG. 27 shows one method of self compensation by curving the receiving electrodes region with a curvature 117 in FIG. 27. The electrodes may also be relatively nonlinear. A product 106 in FIG. 27 which is laterally displaced will have more signal coupled into it due to its closer proximity to transmitting electrode 103 in FIG. 27. However the curvature 117 in FIG. 27 results In a greater distance between the receiving electrodes 108 and the top product surface 105 in FIG. 27. Therefore, careful choice of curved profile 117 can result in a self compensating system requiring relatively little or no software compensation. The curved profile 117 of FIG. 27 may be rigid, or alternatively may be adjustable by manually tensioning a flexible substrate holding electrodes 108 and 109. Receiving electrodes 108 may be split as shown in FIG. 27, or joined into a single, self compensated electrode.

Figure 28:
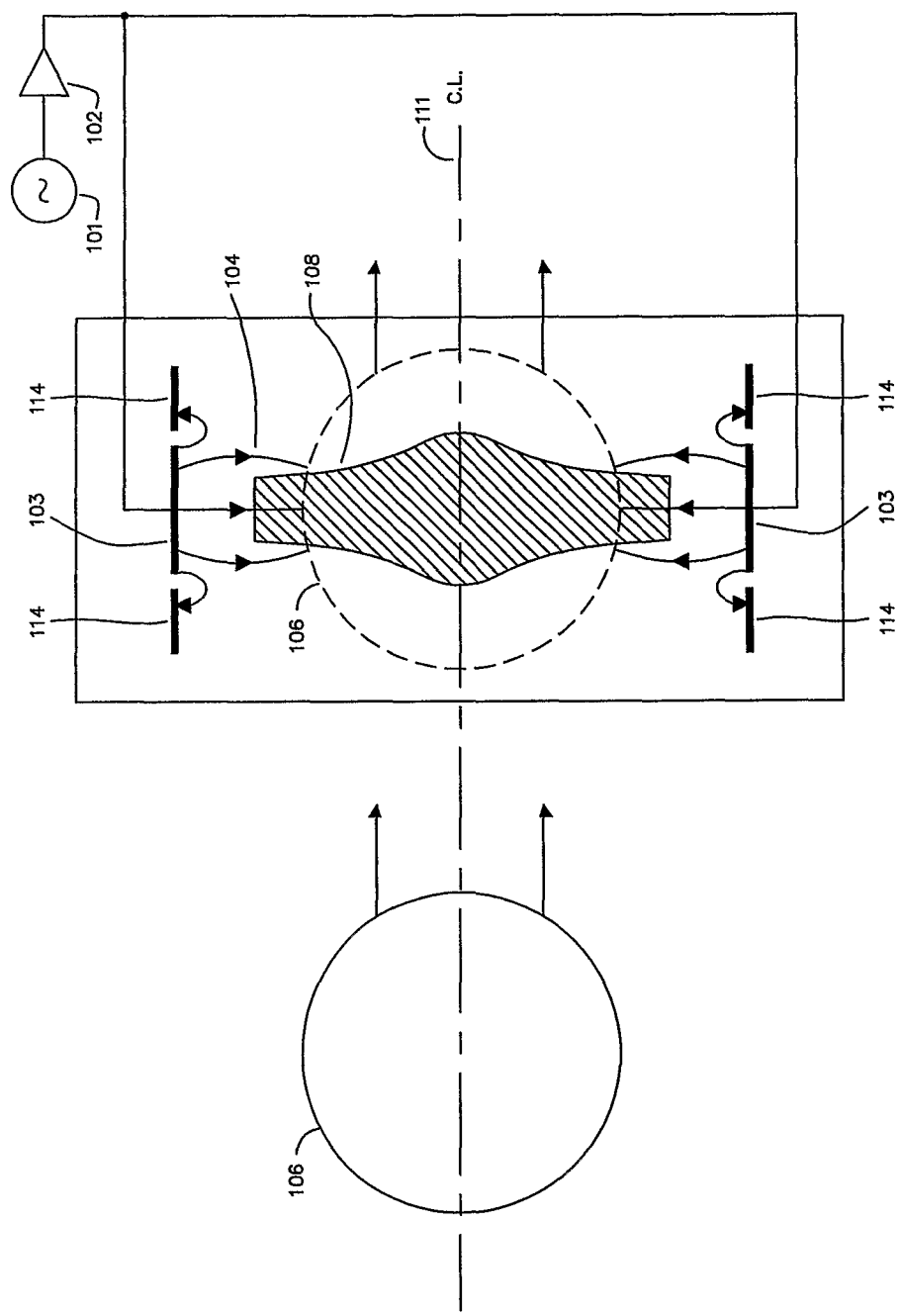
FIG. 28 shows an embodiment of invention for detecting fill or product level in a container, having one receiving electrode and a non-rectangular shape for self compensation.

FIG. 28 shows a second method of compensation achieved by using a relatively non-rectangular receiving electrode 108 in FIG. 28. Careful choice of the profile of electrode 108 in FIG. 28 can also result in a self compensating system requiring no software compensation. The effect of non-rectangular electrode 108 in FIG. 28 may be achieved using an oversize receiving electrode 108 together with a concentric earthed mask immediately alongside. This allows the optimum non-rectangular profile to be provided in cases where several different products are inspected.

The methods described above and illustrated in FIGS. 27 and 28 may be combined to give the optimum self compensation. In this case the receiving electrodes 108 are no longer planar but have a three dimensional profile dependent on the geometry of the product being inspected.

5.1.8 Means for Evaluating the Inspected Product

The results of the inspection are compared with a programmable decision boundary as represented by 310 in FIG. 25. Results 303-305 on one side of the decision boundary 310 are considered acceptable. Results 307-309 on the other side of the decision boundary 310 are considered unacceptable. Products generating these unacceptable results are typically rejected by a mechanical or pneumatic reject mechanism.

Decision boundary 310 is not fixed but can be adjusted depending on the level of scrutiny required.

For self compensating topologies the decision boundary may simply be a line or simple threshold.

5.2 Advantages over other Methods 5.2.1 No Radiation Source

The invention described here relies on relatively low level electric fields. It does not require a radiation source such as gamma or x-ray. No special handing precautions are required when near or servicing this invention.

5.2.2 Immunity to Optical Variations

The invention here is relatively immune to several optical variations that can interfere with vision based technologies. These include any or any combination of:

Immunity to variations in light sources
Immunity to variations in package optical density and colour
Immunity to vibration;
Immunity to dust;
Immunity to packaging graphics
Immunity to labels and tamper proof sleeves 5.2.3 Continuum of Measurement The fill extent is only quantised late during final A/D conversion of the analog signal. Some technologies send multiple rays through sideways to ascertain the fill extent, resulting in a quantised measurement.

5.2.4 Nonlinear in an Advantageous way (for Liquids)

For liquid products, the received signals are nonlinear in an advantageous way. i.e. for a small percentage change in liquid level at the top of the container, a relatively large percentage change occurs in the received signal.

5.2.5 Minimal change to Existing Equipment

This embodiment may be mounted over the top of an existing conveyor. The advantage is fewer product transitions and easier installation.

5.2.6 Inspect towards the end of the Production Line

This embodiment may be used to inspect relatively late in the production line, for example when individual items are in their shipping carton. The later the inspection, the wider variety and greater number of defects that can be detected. For example, a slowly leaking container is difficult to detect at the filling point but relatively easy to detect after the contents have had opportunity to leak out of the container.

5.3 Second PCIS Embodiment 5.3.1 Measure with another Sensor E.G. Laser Inferometer One alternative to the compensation described above is to measure the lateral displacement using a separate sensor, such as a laser inferometer, and use the measured displacement to apply compensation to the received signal. In that case only one receiving electrode covering the entire span may be sufficient.

FIGS. 29a to 29e illustrate alternative embodiments to the arrangement illustrated in FIGS. 22a, 22b and 23. Basically, the detector arrangement is oriented at an angle to the path of the container package being detected.

Figure 29A:
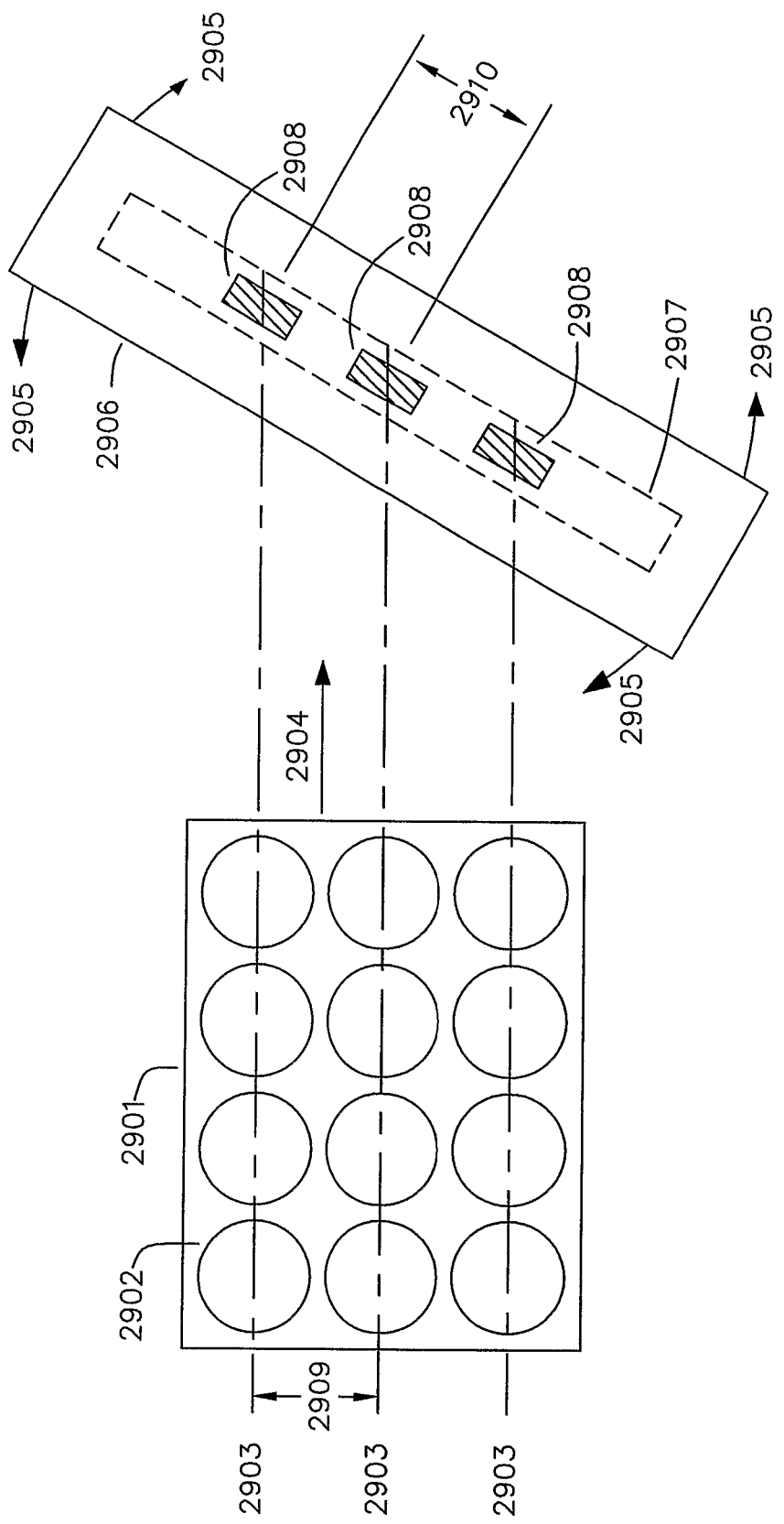
FIGS. 29a to 29g illustrate various embodiments of the invention for arranging electrodes relative to movement of packages and/or containers.

In FIG. 29a, the container package 2901 contains a number of containers 2902, each of which usually has a centre line 2903 indicating the expected movement of the containers. The centre lines 2903 have a distance or pitch 2909 between each other. Arrow 2904 shows the direction of travel of the package 2901. Arrows 2905 show the orientation of the detector head arrangement 2906. The head 2906 has one or more transmitting electrode(s) 2907 and one or more receiver electrodes 2908. The electrodes have a distance 2910 between each other. An advantage of this embodiment is that the effect of the rotation and/or orientation is to substantially align at least one of the electrodes 2907 and/or 2908 relative to the centre line 2903 of the containers. This is accomplished by rotating or orienting the electrodes 2907 or 2908 effective changes the pitch of the distance 2910 to substantially match the container centre line distance 2909. Once aligned, the head 2906 may be relatively fixed in position, at least for the particular container package.

In the embodiment illustrated in FIG. 29a, the receiver electrodes, which have a spacing 2910 between the electrodes 2908 which is larger than the distance 2909 between the centre lines 2903, can be made to align with the centre line spacing 2903 by virtue of the rotation 2905 of the electrodes 2907 and/or 2908. A further advantage is that the embodiment disclosed can be used for packages which have a number of differently sized containers. When the containers are smaller or larger, the head 2906 or electrodes 2907 and/or 2908 may be oriented to substantially align with the centre line of the containers 2903. For example, in FIG. 29a, if the head 2906 is rotated clockwise, the electrodes 2908 would be effectively be aligned for a more closely spaced centre line 2909, whereas, if the head 2906 is rotated anticlockwise, the alignment would be arranged effective for a greater spacing 2909. The pivot of rotation may be central or offset, to match the datum used to align the packages. Multiple heads 2906 (not shown) may also be provided to align electrodes with containers of varying or different centre line spacing.

Figure 29B:
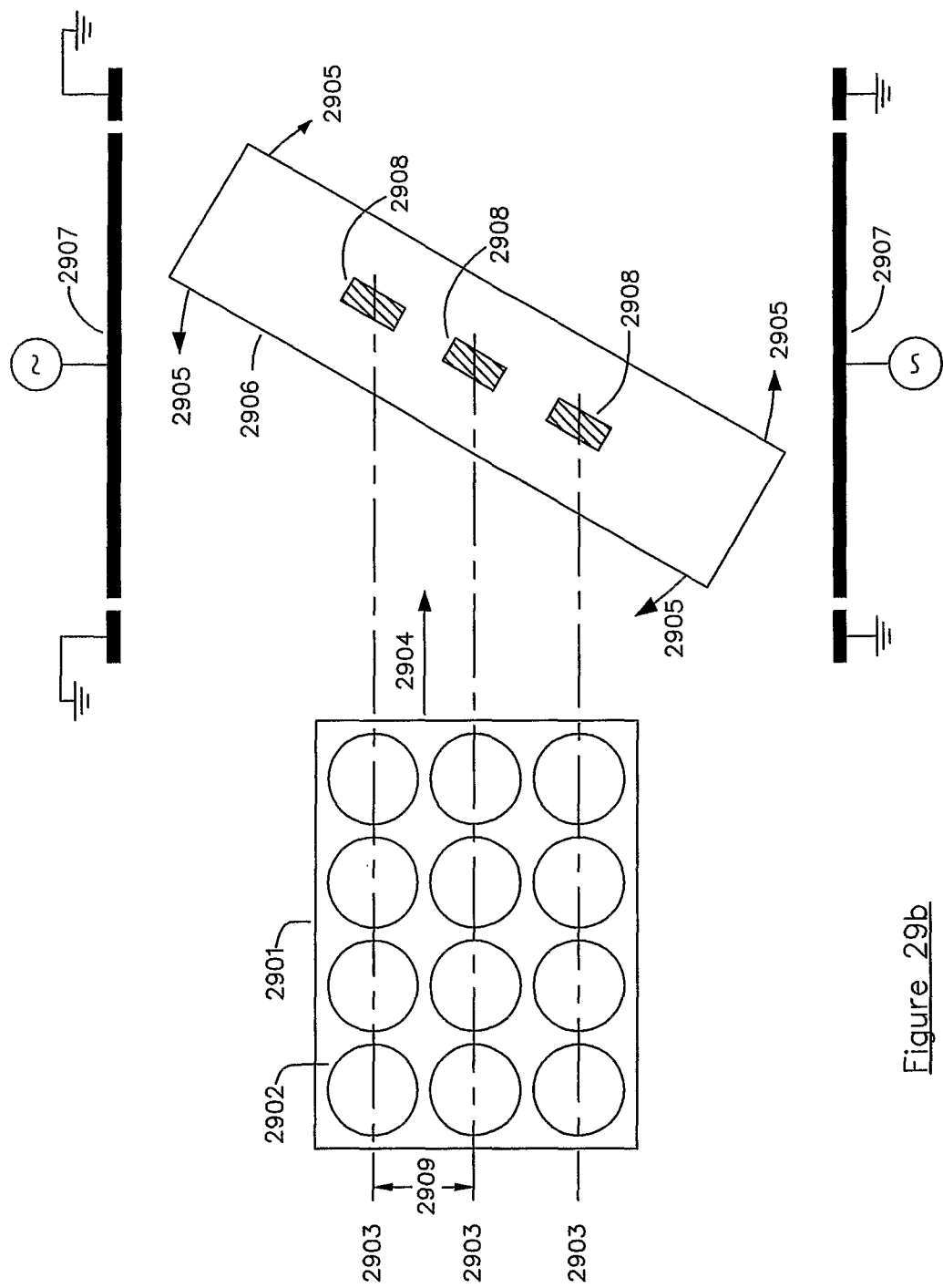

FIG. 29b illustrates a similar arrangement to FIG. 29a, but the transmitting electrodes 2907 are disposed on the side of the package 2901, and the receiver electrodes 2908 are disposed above and/or below the package 2901. In an alternative configuration (not shown), preferably where there are multiple layers of containers 2902, a head 2906 may be disposed both above and below the package 2901, each head being adapted to 'read' a layer of containers 2902.

FIG. 29c again illustrates a similar arrangement to FIG. 29a, but the transmitting electrodes 2907 are disposed proximate the head 2906, and are aligned with the orientation of the head 2906, and arranged to be provided proximate one or more sides of the package 2901. Alternatively, the electrodes 2907 may be disposed above and/or below the package 2901.

Figure 29C:
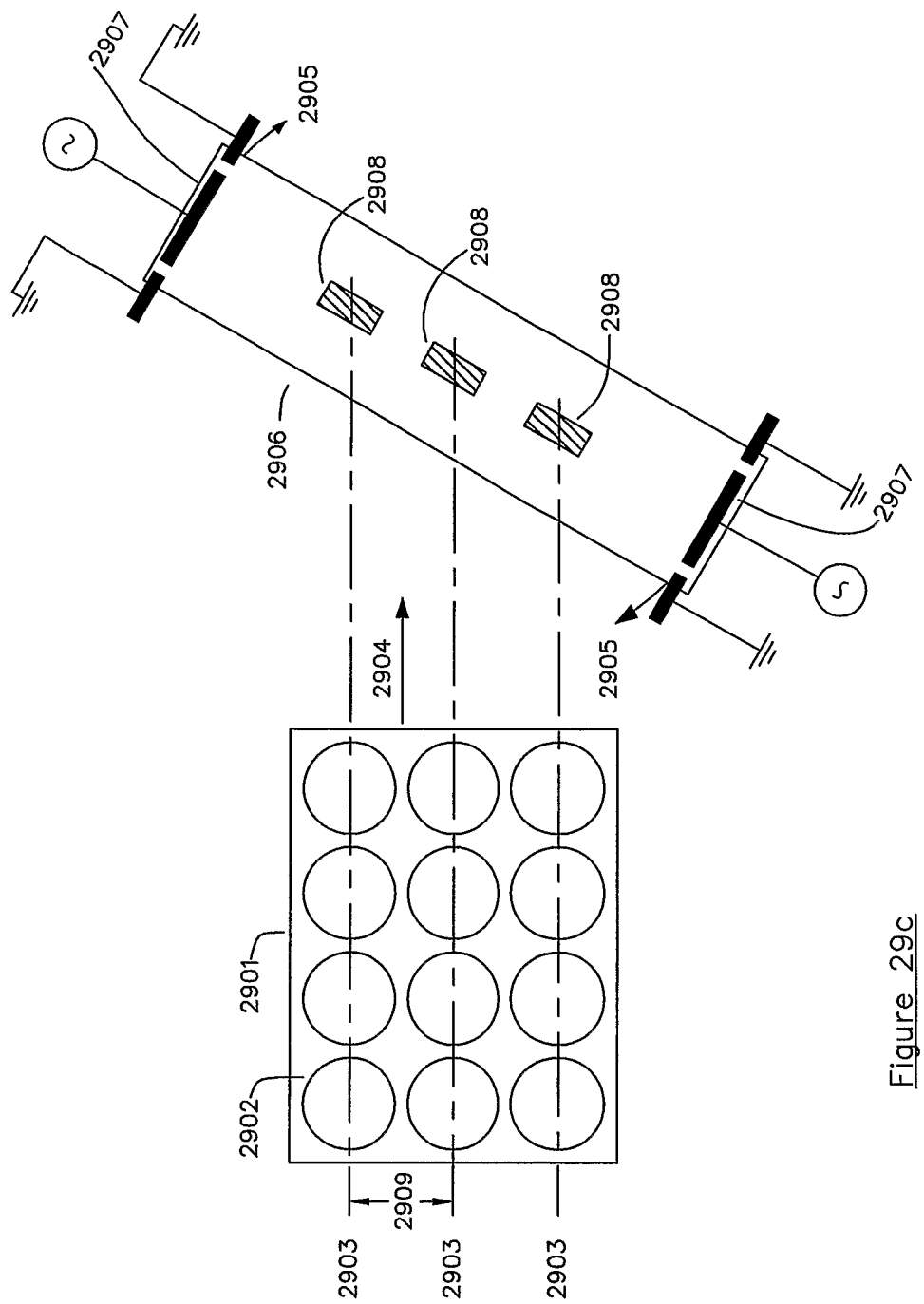
Figure 29D:
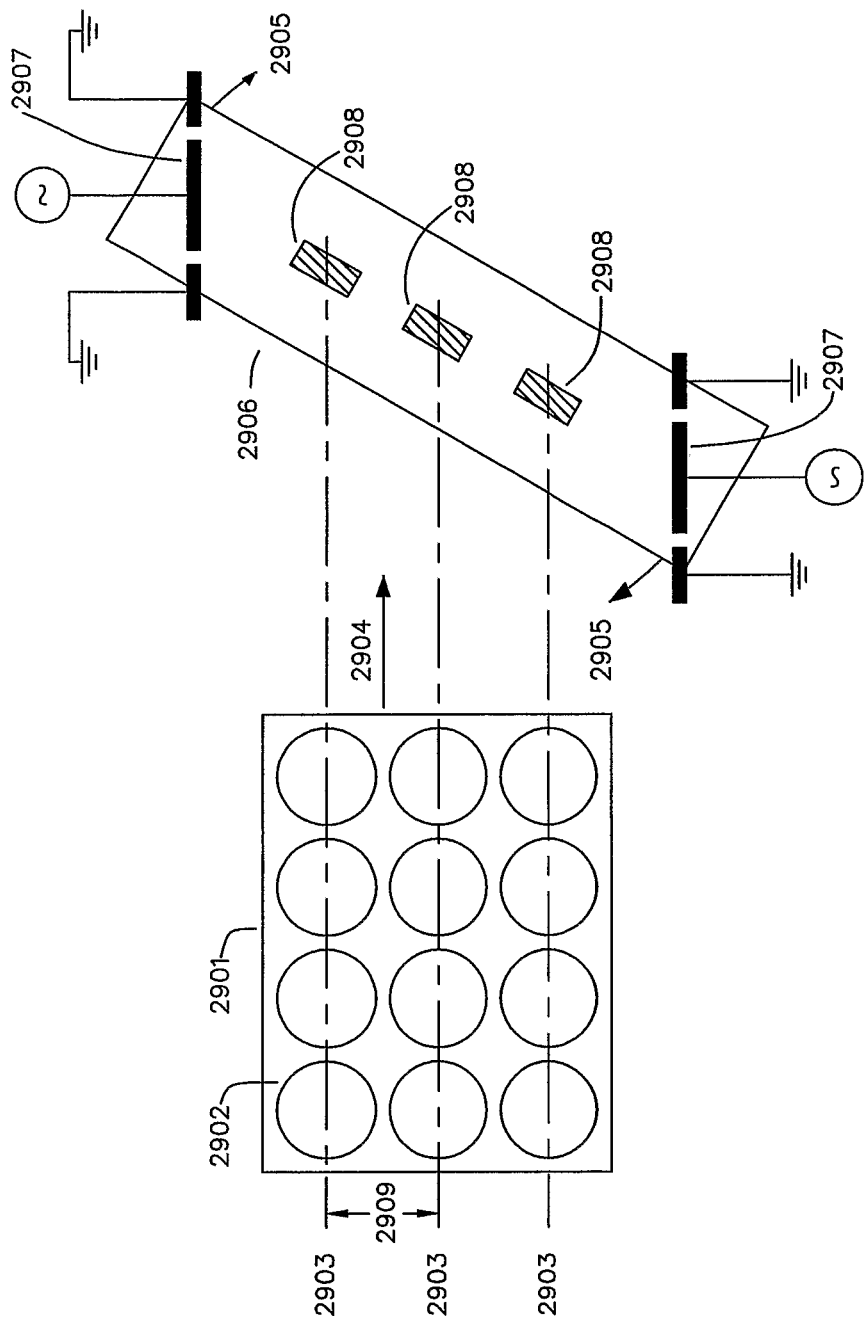

In FIG. 29d, the arrangement is similar to FIG. 29c, but the transmitting electrodes are disposed substantially parallel to the movement 2904 of the package 2901.

Figure 29E:
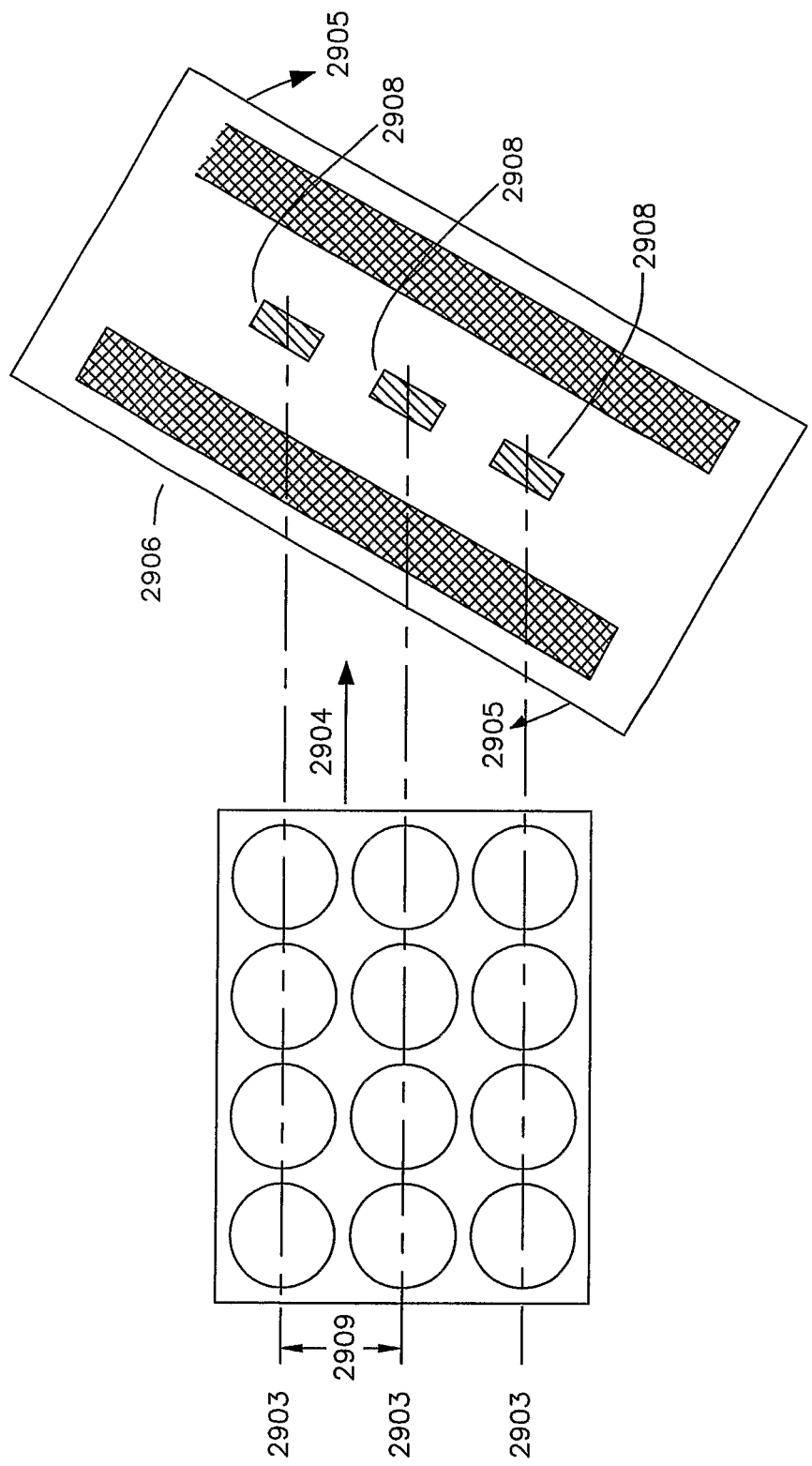

In FIG. 29e, the arrangement is similar to that of FIG. 29a, but the head 2906 has multiple transmitting electrodes 2907 disposed proximate the head 2906 and multiple receiver electrodes 2908. Preferably, the transmitting electrodes 2907 are disposed in a similar plane to the receiver electrodes 2908.

Figure 29F:
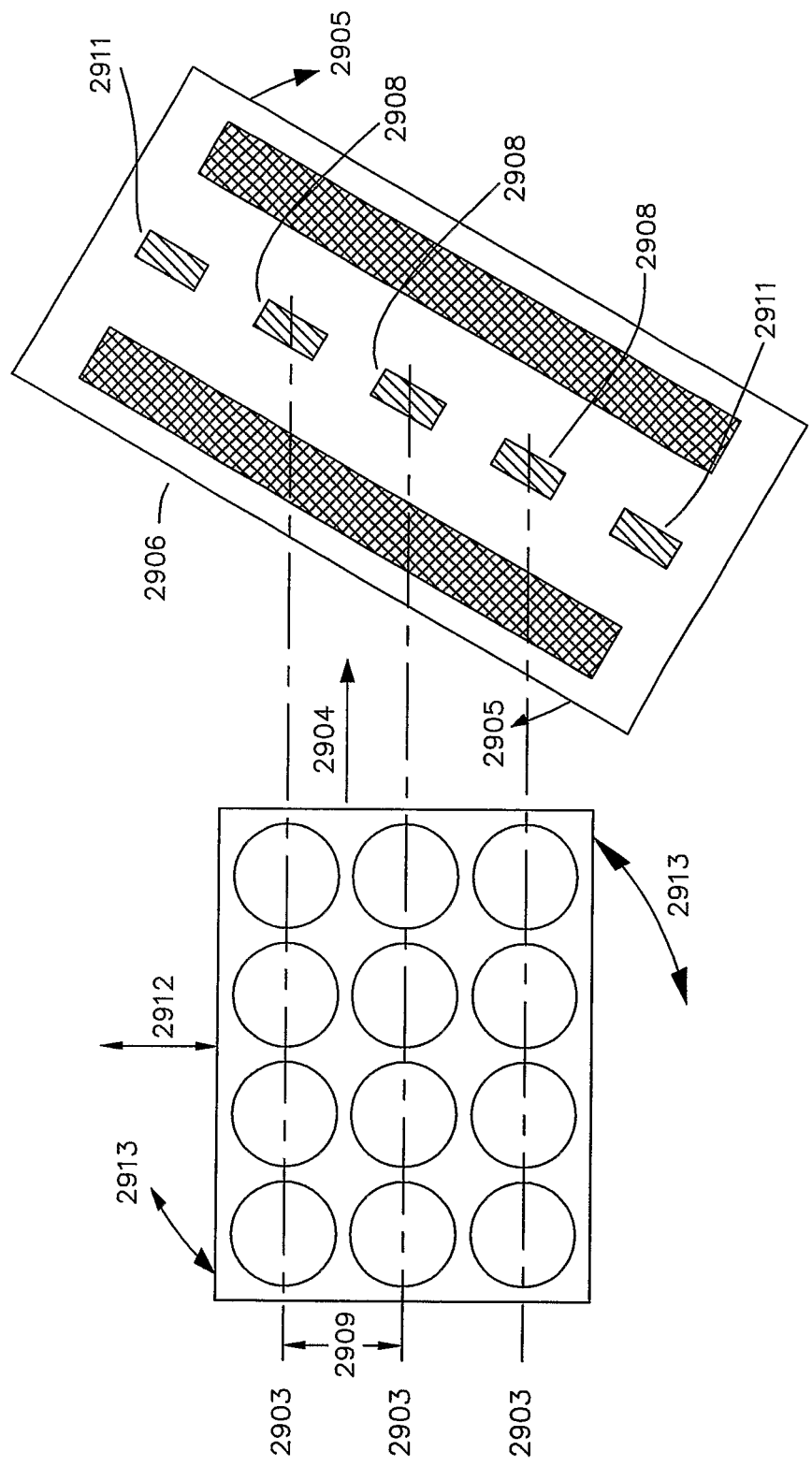

FIG. 29f shows the addition of two outer receiver electrodes 2911, used to detect lateral misalignment 2912, skewing 2913, or gauge package size (overall diameter). The information gained from these outer two electrodes may be used to compensate the inner electrode signals 2908 for the effects of lateral misalignment or skewing. When used to detect under/over diameter packages this information may be used in a feedback capacity to control the rotation 2905 and hence the effective inspection pitch. This concept may equally be applied to all FIGS. 29a through 29e.

Figure 29G:
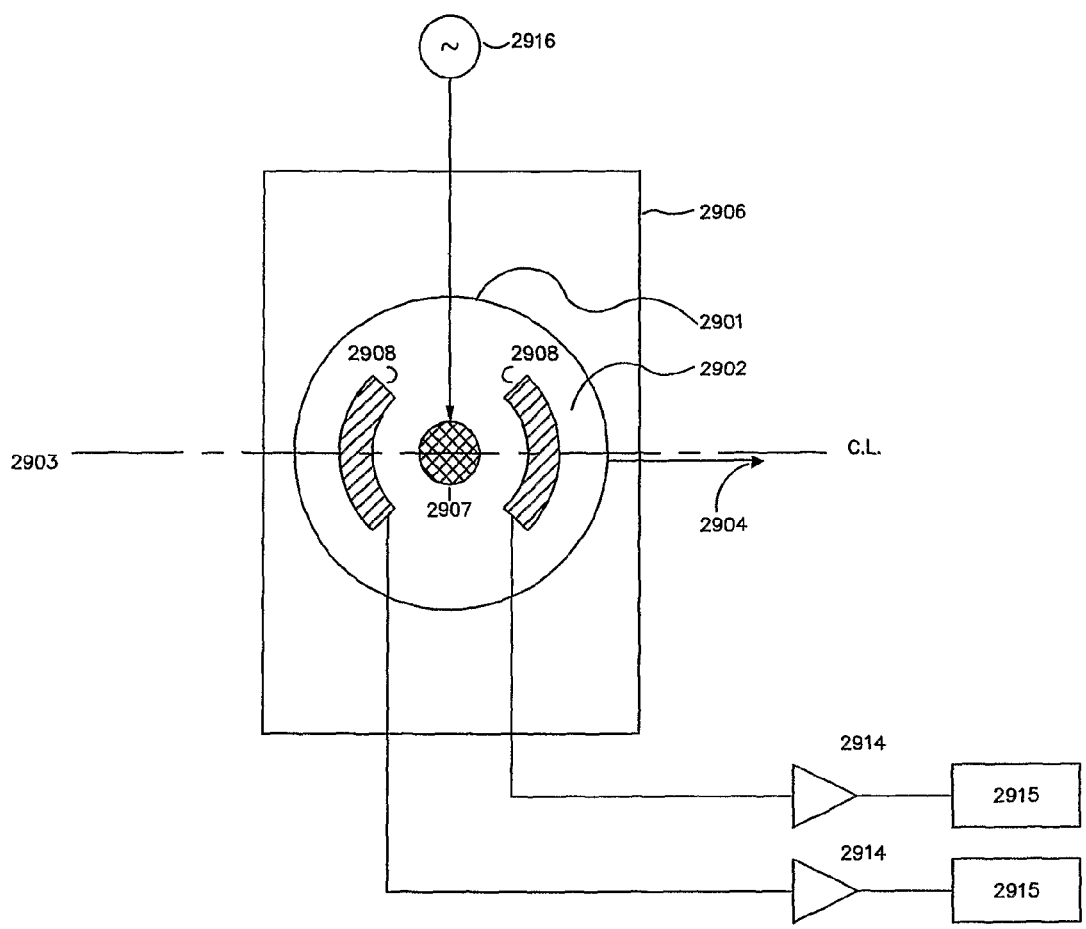

FIG. 29g shows an arrangement suitable for inspecting canned product just prior to lid closing. Here a tin or can 2902 containing product 2914 to level 2915 passes under the scanning head assembly 2906. Transmitting electrode 2907 creates a field which is sensed by one or more receiving electrodes 2908. The product 2914 and its associated fill level 2915 affect the signal from receiving electrodes 2908. Preferably, at least one of the electrodes is shaped corresponding substantially to the shape of the product to be detected. For example, an electrode used to detect circular food products, may be shaped substantially, or at least partially, circular. Furthermore, one or more electrodes may be provided in order to correspond to the product 'shape'. For example, in FIG. 29g, more receiver electrodes may be provided in a relatively circular shape to correspond with a relatively circular product. The same may apply to transmitter electrodes.

Figure 30:
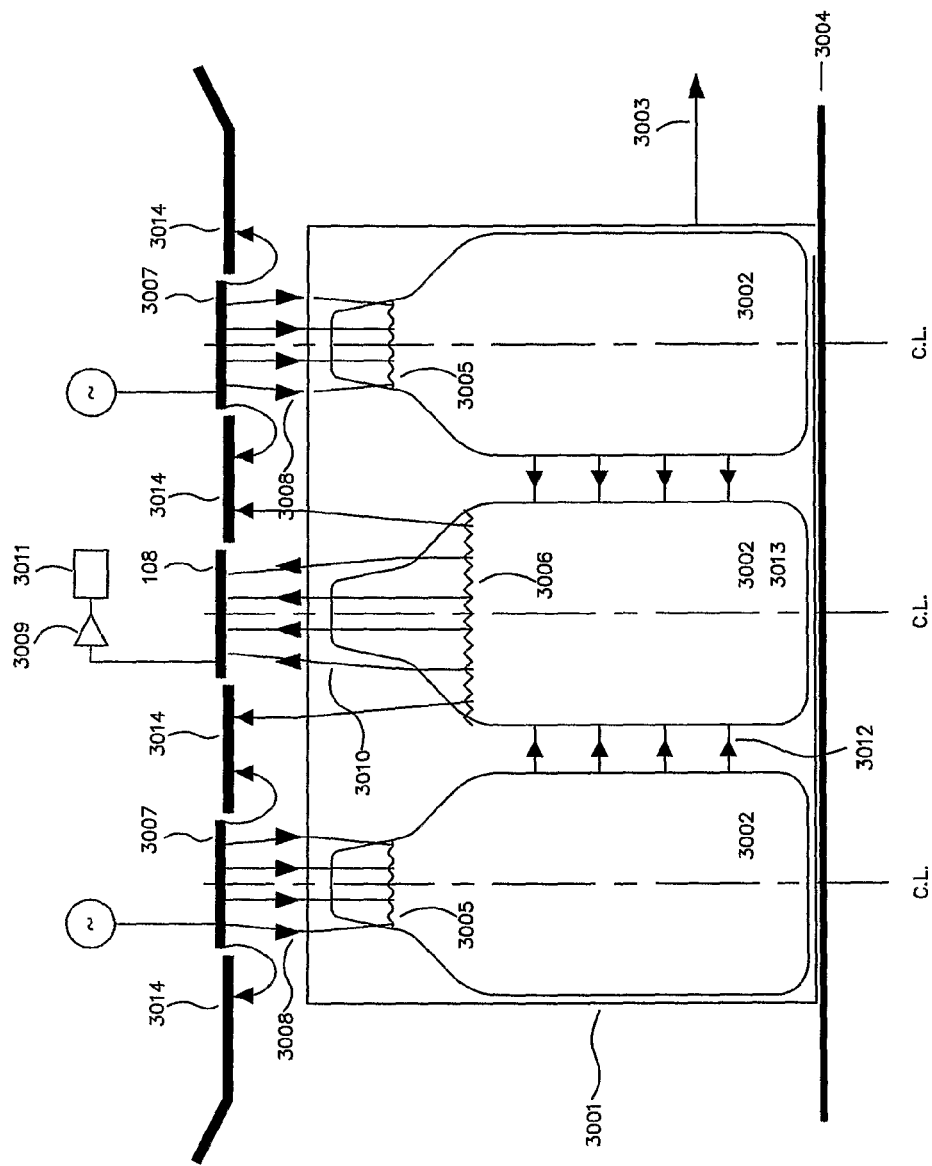
FIG. 30 illustrates an embodiment of invention in which one or more containers are coupled to provide a detection signal.

FIG. 30 illustrates a further alternative arrangement. A package 3001 having one or more containers 3002 is arranged to travel in a direction of movement 3003 on a conveyer arrangement 3004. The present invention is adapted to detect one or more characteristics (as herein disclosed) of the container, such as fluid level 3005 and/or 3006 in order to detect, for example, a low level of fluid 3006.

The arrangement of FIG. 30 illustrated has one or more signal transmitting electrodes 3007 disposed substantially aligned with the centre line CL of a container 3002. The arrangement may be adapted to accommodate one or more containers in which case the electrodes are aligned corresponding to the expected container position. The transmitter 3007 serves, in operation, to radiate a field 3008 which impinges on the container 3002 and/or its contents. The signal, in effect, permeates the container and/or its contents and the receiver electrode 3009 receives a signal 3010. The signal 3010 is then processed 3011 to provide an indication of the characteristic, such as fluid level 3005. In the event that there is more than one container, such as container 3002 and 3013, the signal 3008 emanates 3012 from container 3002, closest to the transmitting electrode 3007, and into container 3013 before being received by the receiver electrode 3009. In this case, the signal 3010 received is in effect a signal representing an average of the containers 3002 and 3013 through which the signal has travelled. The receiver electrode is also preferably aligned with one of the containers 3002 and/or 3013. One advantage of this arrangement is that the electrodes 3007 and 3008 may be disposed on one side of the containers 3002, for example disposed above the direction of movement 3003. Another advantage of coupling more than one container at a time, as is illustrated in FIG. 30, is that a better coupling to the container and there contents is provided, and thus enables an improved detection of a characteristic.

In the embodiments illustrated in this specification, any number of heads and/or electrodes may be provided in accordance with a particular application of the invention.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims; means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" when used in this specification is taken to specify the presence of stated features, integers, steps or components but does not preclude the presence or addition of one or more other features, integers, steps, components or groups thereof." Thus, unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

The invention claimed is:

1. A detection apparatus for an inspection line arrangement, comprising:
  a detection zone on the inspection line through which a plurality of targets, each having at least one characteristic to be inspected, can pass concurrently, or a target having multiple characteristics to be inspected can pass, the detection zone being provided operatively by:
  a signal source or a signal receiver disposed in a first transmitting or receiving surface,
  a complementary signal receiver, which is complementary to the signal source, or a complimentary signal source, which is complementary to the signal receiver, disposed in a second complementary receiving or complementary transmitting surface, and a linearizing surface provided proximate the signal receiver, and provided at or near a potential of the signal receiver, the linearizing surface being operative in combination with the signal receiver to resolve detail of the target in a linear slice, and a movement structure for concurrently moving the target with multiple characteristics or the multiple targets with at least one characteristic to be inspected, relative to the signal receiver, through the inspection zone, wherein the first surface plane is disposed at an angle relative to the second surface plane, which angle is not equal to 0 degrees or 360 degrees, and the first surface plane and the second surface plane are disposed to provide, operatively, said detection zone, wherein the apparatus inspects the target or the plurality of targets while the target or the plurality of targets is/are moving relative to the signal receiver via the movement structure, wherein the plurality of targets or the multiple characteristics of a target are inspected in the detection zone.

2. An apparatus as claimed in claim 1, wherein a characteristic or characteristic(s) of target(s) in the detection zone is detected and wherein the characteristic(s) is any one or any combination of:
Presence/absence
Count
Fill level/Head Space
Location/Registration
Orientation
Shape/Profile
Density/Electrical Permittivity/Conductivity
Bridging
Isolation
Electrical Leakage
Presence or absence of fluid
Fluid leakage or dampness
Resistance, capacitance, and/or impedance,
Integrity,
Density,
Continuity
Distribution
Doping
Enhancement,
Indicia, wherein the indicia is a barcode and/or a data matric, and
Other measurable physical attributes of the target(s).

3. An apparatus as claimed in claim 1, wherein the signal source operates at a frequency substantially at any one of:
substantially 5 kHz to 1 MHz,
substantially 100 kHz to 1 MHz, substantially 100 kHz to 10 MHz, and
substantially 300 kHz.

4. An apparatus as claimed in claim 1, wherein the function of signal source and signal receiver alternates at any one of:
substantially 5 Hz to 100 Hz,
substantially 100 Hz to 5 kHz,
substantially 500 times per second.

5. An apparatus as claimed in claim 1, wherein the first surface plane is movable with respect to the second surface plane.

6. An apparatus as claimed in claim 1, wherein the first surface plane and/or second surface plane comprises at least one electrode shaped corresponding substantially to the shape of the target.

7. An apparatus as claimed in claim 1, wherein the first surface plane comprises an array of signal sources or signal receivers.

8. An apparatus as claimed in claim 1, wherein the second surface plane comprises an array of signal sources or signal receivers complimentary to the first surface plane.

9. A method of providing detection of a plurality of targets, each having at least one characteristic to be inspected, or a target having multiple characteristics to be inspected, within a detection zone of an inspection line arrangement, the method comprising the steps of:

providing a signal source or a signal receiver disposed in a first transmitting or receiving surface, providing a complementary signal receiver, which is complementary to the signal source, or a complementary signal source, which is complementary to the signal receiver, disposed in a second transmitting or receiving surface, providing a linearizing surface proximate the signal receiver, said linearizing surface being provided at or near the potential of the signal receiver, the linearizing surface being operative in combination with the signal receiver to resolve detail of the target in a linear slice, disposing the first surface at an angle relative to the second surface, which angle is not equal to 0 degrees or 360 degrees, and enabling the first surface and the second surface to provide, operatively, the detection zone, concurrently moving the target with multiple characteristics or the multiple targets with at least one characteristic to be inspected, relative to the signal receiver, through the inspection zone, and inspecting the target with multiple characteristics or the multiple targets with at least one characteristic in the detection zone.

10. A method as claimed in claim 9, wherein the first surface plane is movable with respect to the second surface plane.

11. A method as claimed in claim 9, wherein the first plane and/or second plane comprises at least one electrode shaped corresponding substantially to the shape of the target.

12. A method as claimed in claim 9, comprising the further step of providing an array of signal sources or signal receivers in first surface plane.

13. A method as claimed in claim 9, comprising the further step of providing a complementary array of signal sources or signal receivers in second surface plane.

14. A method as claimed in claim 9, wherein a characteristic or characteristic(s) of target(s) in the detection zone is detected and wherein the characteristic(s) is any one or any combination of:
Presence/absence
Count
Fill level/Head Space
Location/Registration
Orientation
Shape/Profile
Density/Electrical Permittivity/Conductivity
Bridging
Isolation
Electrical Leakage
Presence or absence of fluid
Fluid leakage or dampness
Resistance, capacitance, and/or impedance,
Integrity,
Density,
Continuity
Distribution Doping
Enhancement,
Indicia, wherein the indicia is a barcode and/or a data matrix, and
Other measurable physical attributes of the target(s).

* * * * *